US012776388B2

(12) United States Patent
Sanborn

(10) Patent No.: US 12,776,388 B2
(45) Date of Patent: Oct. 27, 2026

(54) SYSTEM AND METHOD FOR VARIANT CALLING

(71) Applicant: NANTOMICS, LLC, Culver City, CA (US)

(72) Inventor: John Zachary Sanborn, Culver City, CA (US)

(73) Assignee: NANTOMICS, LLC, Culver City, CA (US)

( * ) Notice: Subject to any disclaimer, the term of this patent is extended or adjusted under 35 U.S.C. 154(b) by 1118 days.

(21) Appl. No.: 17/429,477

(22) PCT Filed: Feb. 27, 2020

(86) PCT No.: PCT/US2020/020047
§ 371 (c)(1),
(2) Date: Aug. 9, 2021

(87) PCT Pub. No.: WO2020/185411
PCT Pub. Date: Sep. 17, 2020

(65) Prior Publication Data

US 2022/0108768 A1 Apr. 7, 2022

Related U.S. Application Data

(60) Provisional application No. 62/815,951, filed on Mar. 8, 2019.

(51) Int. Cl.
*G16B 20/20* (2019.01)
*G06F 16/25* (2019.01)
(Continued)

(52) U.S. Cl.
CPC ........... *G16B 20/20* (2019.02); *G06F 16/258* (2019.01); *G06F 16/9024* (2019.01); *G16B 30/10* (2019.02); *G16B 50/10* (2019.02)

(58) Field of Classification Search
None
See application file for complete search history.

(56) References Cited

U.S. PATENT DOCUMENTS

2012/0041683 A1 2/2012 Vaske et al.
2016/0101170 A1 4/2016 Hacohen et al.
(Continued)

OTHER PUBLICATIONS

International Preliminary Report on Patentability for International (PCT) Patent Application No. PCT/US20/20047, dated Sep. 23, 2021 7 pages.

(Continued)

*Primary Examiner* — Karlheinz R. Skowronek
*Assistant Examiner* — Mary C Leverett
(74) *Attorney, Agent, or Firm* — Sheridan Ross P.C.

(57) ABSTRACT

A locus tester or locust database has stored therein DNA or RNA sequence information for one or more loci of interest. The sequence information may include a list of k-mers in a given DNA or RNA sequence, an identification of whether each k-mer in the list of k-mers appears in a reference sequence or in a variation of the reference sequence, and a count of how many times each k-mer in the list of k-mers has been identified in sequence information for the locus of interest in question. Sequence data for the locus in question received from a data source may be broken into fragments, with each fragment containing one or more k-mers. These k-mers may be quickly compared to the list of k-mers in the locust database to determine whether the sequence data corresponds to the reference sequence or to a variation of the reference sequence.

20 Claims, 17 Drawing Sheets

Specification includes a Sequence Listing.

(51) Int. Cl.
*G06F 16/901* (2019.01)
*G16B 30/10* (2019.01)
*G16B 50/10* (2019.01)

(56) References Cited

U.S. PATENT DOCUMENTS

| | | | | |
|---|---|---|---|---|
| 2017/0032103 A1* | 2/2017 | Nguyen | ................. | C12Q 1/708 |
| 2017/0286594 A1* | 10/2017 | Reid | ....................... | G16B 45/00 |
| 2018/0237949 A1 | 8/2018 | Sanborn | | |

OTHER PUBLICATIONS

K-mers, Wikipedia, 6 pages.
De Bruijn graph, Wikipedia , 5 pages.
"NantOmics Acquires Genos To Bolster Its Precision Medicine Platform," Genos, Apr. 13, 2017, 2 pages.
Souza et al., "Evaluation of the cytotoxic response mediated by perforin and granzyme B in patients with non-Hodgkin lymphoma," Leukemia & Lymphoma, 2018, vol. 59(1), http://dx.doi.org/10.1080/10428194.2017.1341978, abstract only, 1 page.
Iqbal et al., "De novo assembly and genotyping of variants using colored de Bruijn graphs," Europe PMC, Author Manuscript, Aug. 1, 2012, pp. 1-17.
Extended European Search Report for European Patent Application No. 20770106.1, dated Jan. 4, 2023 9 pages.
International Search Report prepared by the United States Patent Office on May 11, 2020, for International Application No. PCT/US2020/020047, 5 pages.
Written Opinion prepared by the United States Patent Office on May 11, 2020, for International Application No. PCT/US2020/020047, 9 pages.

* cited by examiner (1) Walk "reads" along reference edges, tag all edges as "REF"

(2) Walk "reads" along Variant graphs to tag *non-reference* kmers with Variant (or Variants)

| kmer | Variant Tag |
|---|---|
| A-TC-C | c.3A>C |
| T-CT-G | c.3A>C |
| A-TA-T | REF |
| T-AT-G | REF |
| A-TG-C | REF |
| A-TG-A | c.5delC |
| T-GA-T | c.5delC |
| C-AT-T | c.9_10insAGGCTATGGT |
| A-TT-A | c.9_10insAGGCTATGGT |
| T-TA-G | c.9_10insAGGCTATGGT |
| T-AG-G | c.9_10insAGGCTATGGT |
| A-GG-C | c.9_10insAGGCTATGGT |
| A-TG-G | c.9_10insAGGCTATGGT |
| ... | |

LOCUST->VARIANT

| Variant ID | Locust ID |
|---|---|
| 1 | 1 |
| 2 | 1 |
| 3 | 1 |
| 4 | 2 |
| 5 | 2 |
| 6 | 3 |
| ... | ... |

LOCUSTS

| Locust ID | Region | Kmer Length |
|---|---|---|
| 1 | 17:1-1000 | 3 |
| 2 | 17:2000-300 | 4 |
| 3 | 12:100000-12000 | 25 |
| ... | | |

PATIENTS

| Patient ID | Tumor Type | Age |
|---|---|---|
| 1 | Breast Cancer | 23 |
| 2 | Lung Cancer | 60 |
| 3 | Leukemia | N/A |
| 4 | Breast Cancer | 49 |
| ... | | |

| Variant ID | Kmer |
|---|---|
| 1 | A-AAT-G |
| 1 | GC-ATC-GG |
| 1 | A-TTT-G |
| 1 | T-ATA-C |
| 1 | C-GGG-A |
| 2 | T-AAAA-C |
| 2 | C-ATCT-G |
| ... | |

KMERS

| Variant ID | Gene | Coding Change | Protein Change |
|---|---|---|---|
| 1 | BRCA2 | c.125G>A | p.R72C |
| 2 | BRCA2 | c.126del | p.P18* |
| 3 | BRCA2 | c.123_124insAGG | p.23_24insP |
| 4 | TP53 | c.125G>A | p.R72C |
| 5 | TP53 | c.254T>C | p.H125R |
| 6 | PIK3CA | c.57_58delinsCC | p.S23fs*25 |
| ... | ... | | |

VARIANTS

*Fig. 7*

| Variant ID | Patient ID | Variant AF |
|---|---|---|
| 1 | 1 | 0.5 |
| 4 | 1 | 0.05 |
| 4 | 2 | 0.1 |
| 2 | 3 | 0.6 |
| 5 | 3 | 1.0 |
| 1 | 4 | 0.2 |

RESULTS

TP53 Results - Somatic

Luciferase reporter constructs of TYMS promoter region polymorphisms. Potential polymorphic 3R and 2R alleles for TSER are shown. The 28 bp tandem repeats are boxed and shown as containing a functional (G; hatched) or non-functional (C; shaded) USF-1 binding site. *Most recently identified polymorphism; wt, wild type.

TYMS results

Allele Frequencies

| Allele | % of Patients (N) | dbSNP* % |
|---|---|---|
| 1RC | 0.03 (1) | n/a |
| 2RGC | 41.33 (1,259) | n/a |
| 2RCC | 0.82 (25) | n/a |
| **2R total** | **42.15 (1,285)** | **42.81** |
| 3RGGC | 29.15 (888) | n/a |
| 3RGCC | 28.63 (872) | n/a |
| 3RCCC | 0.03 (1) | n/a |
| **3R total** | **57.81 (1,761)** | **56.02** |
| **4R+** | **Not Tested** | **1.17** |

* dbSNP rs45445694 build 150

*Fig. 14*

TYMS results

Genotype Frequencies

| Genotype | % of Patients (N) | Study* % (N) |
|---|---|---|
| 2RGC \| 3RGGC | 23.55 (442) | 16.9 (10) |
| 2RGC \| 3RGCC | 22.91 (430) | 32.2 (19) |
| 2RGC \| 2RGC | 19.98 (375) | 18.6 (11) |
| 3RGCC \| 3RGGC | 14.38 (270) | 8.5 (5) |
| 3RGGC \| 3RGGC | 9.22 (173) | 5.1 (3) |
| 3RGCC \| 3RGCC | 8.52 (160) | 10.2 (6) |
| 2RCC \| 2RGC | 0.64 (12) | 1.7 (1) |
| 2RCC \| 3RGCC | 0.53 (10) | 5.1 (3) |
| 2RCC \| 3RGGC | 0.16 (3) | 1.7 (1) |
| 1RC \| 3RGCC | 0.05 (1) | Not Tested |
| 3RCCC \| 3RGCC | 0.05 (1) | Not Tested |

* Lincz et al 2007, a study of TYMS genotypes in 59 colorectal cancers (Caucasian population in Australia)

NOTE: 2RCC variant is believed to be non-functional, and homozygous 2RCC may be “incompatible with life”. No 2RCC | 2RCC genotypes were identified.

*Fig. 15*

SYSTEM AND METHOD FOR VARIANT CALLING

CROSS-REFERENCE TO RELATED APPLICATIONS

This application is a national stage application under 35 U.S.C. § 371 and claims the benefit of PCT Application No. PCT/US2020/020047 having an international filing date of 27 Feb. 2020, which designated the United States, and which PCT application claims the benefit of priority under 35 U.S.C. § 119(e) to U.S. Provisional Patent Application 62/815,951, filed 8 Mar. 2019. The entireties of each of the above-referenced applications are incorporated herein by reference.

REFERENCE TO SEQUENCE LISTING

This application contains a Sequence Listing submitted as an electronic ST.25 txt file named "10009_5_PCT_SEQ_Listing_ST25.txt", having a size in bytes of 7724 bytes, and created on Apr. 16, 2020. The information contained in this electronic ST.25 txt file is hereby incorporated by reference in its entirety.

FIELD OF THE DISCLOSURE

The field of the invention is variant calling of genomic or transcriptomic sequence data at a locus of interest.

BACKGROUND

The background description includes information that may be useful in understanding the present inventive subject matter. It is not an admission that any of the information provided herein is prior art or applicant admitted prior art, or relevant to the presently claimed inventive subject matter, or that any publication specifically or implicitly referenced is prior art or applicant admitted prior art.

The ability to deliver personalized medical treatment depends on being able to identify, within a reasonable amount of time, personal attributes relevant to that medical treatment, and then to categorize those personal attributes accurately so that an appropriate treatment may be selected. Known systems and methods for identifying and categorizing genomic or transcriptomic sequence data at a locus of interest require extensive processing power and a significant amount of time. As a result, they cannot be used to deliver personalized medical treatment on a meaningful scale.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Thus, there is still a need to be able to rapidly and reliably identify variant sequences at a locus of interest in an individual. For example, it is important to identify known or recurrent somatic mutations in genes that are critical in disease states, such as KRAS or TP53. In addition, the ability to quickly identify germline variants that are pathogenic or that carry an increased risk of being pathogenic, such as BRCA1 and BRCA2, is important for diagnosis and treatment of patients. Similarly, the ability to accurately call variants that are difficult to identify with current methods, such as variants in the TYMS VNTR region or the BRCA2 c. 156_157insAlu rearrangement, is important.

SUMMARY

Described herein are apparatuses, systems, and methods for variant calling (i.e. identification of variant sequences) of genomic or transcriptomic sequence data at a locus of interest, by expressing the sequence data at the locus of interest in the format of a de Bruijn graph; breaking the sequence data in de Bruijn graph format into at least two predetermined fragments, where each fragment comprises at least two k-mers; matching the sequence data fragments against a database describing a genomic or transcriptomic locus of interest; and calling the sequence data as a variant sequence with which the sequence data has the highest count of k-mers. The database describing a genomic or transcriptomic locus of interest may include sequence information for a reference sequence of the locus in the format of a de Bruijn graph and sequence information for at least one variant sequence of the locus in the format of a de Bruijn graph. The sequence information for at least one variant sequence of the locus may include the at least two predetermined fragments. Each fragment may include at least two k-mers, and each fragment may be unique and specific to the at least one variant.

The sequence data may be genomic sequence data. The sequence data may be transcriptomic sequence data. At least one variant sequence of the locus may be de-identified. The at least one variant sequence may be selected from the group consisting of single nucleotide variants, multiple nucleotide variants, insertions, deletions, gene fusions, and haplogroups.

In some embodiments, junction k-mers in the sequence data or the sequence information may be identified. A relative support at the identified junction k-mers may be calculated.

Also described herein are databases describing a genomic or transcriptomic locus of interest. The database includes first sequence information for a reference sequence of a locus in the format of a de Bruijn graph and second sequence information for at least one variant sequence of the locus in the format of a de Bruijn graph. The sequence information for at least one variant sequence of the locus comprises at least two fragments. Each fragment is unique and is specific to the at least one variant.

The database may include a list of k-mer junctions, and may also include a list of k-mers appearing in the first sequence information and the second sequence information. The database may include a count corresponding to each k-mer in the list of k-mers, where the count corresponds to the number of occurrences of the each k-mer in the first and second sequence information. The database may include a variant tag corresponding to each k-mer in the list of k-mers. At least some of the variant tags may identifying the corresponding k-mers with the reference sequence. At least some of the variant tags may identify the corresponding k-mers with a single nucleotide variant, a multiple nucleotide variant, an insert, a deletion, a gene fusion, or a haplogroup.

Also described herein are servers that include a database interface; a processor coupled with the database interface; and computer memory coupled with the processor. The computer memory stores instructions that, when executed by the processor, enable the processor to: receive genomic sequence data from a data source; format the genomic sequence data into a de Bruijn graph; break the sequence data in the de Bruijn graph format into at least two predetermined fragments; prepare a database call for transmitting via the database interface, wherein the database call comprises a call for sequence information for a reference sequence of a locus of interest in the format of a de Bruijn graph; receive the sequence information via the database interface; compare the at least two predetermined fragments with at least a portion of the reference sequence of the locus of interest; and generate a report that includes results of the comparison of the at least two predetermined fragments with the at least a portion of the reference sequence of the locus of interest.

The sequence information may include at least one variant sequence of the locus of interest. The sequence information may include a list of k-mers and a count for each k-mer in the list of k-mers. The comparing may include identifying matches between a set of k-mers int eh at least two predetermined fragments and one or more k-mers in the list of k-mers. The report may identify the sequence data as corresponding to the reference sequence or the variant sequence based on the matching. The computer memory may comprise additional instructions that, when executed by the processor, further enable the processor to transmit the sequence data via the database interface.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The present disclosure is described in conjunction with the appended figures, which are not necessarily drawn to scale:

FIG. 7 illustrates a relational locust database in accordance with at least some embodiments of the present disclosure;

FIG. 14 shows the allele frequencies in clinical data samples of tumor and normal DNA files run against a locust database in accordance with at least some embodiments of the present disclosure;

FIG. 15 shows the genotype frequencies in clinical data samples of tumor and normal DNA files run against a locust database in accordance with at least some embodiments of the present disclosure;

DETAILED DESCRIPTION

Figure 1:
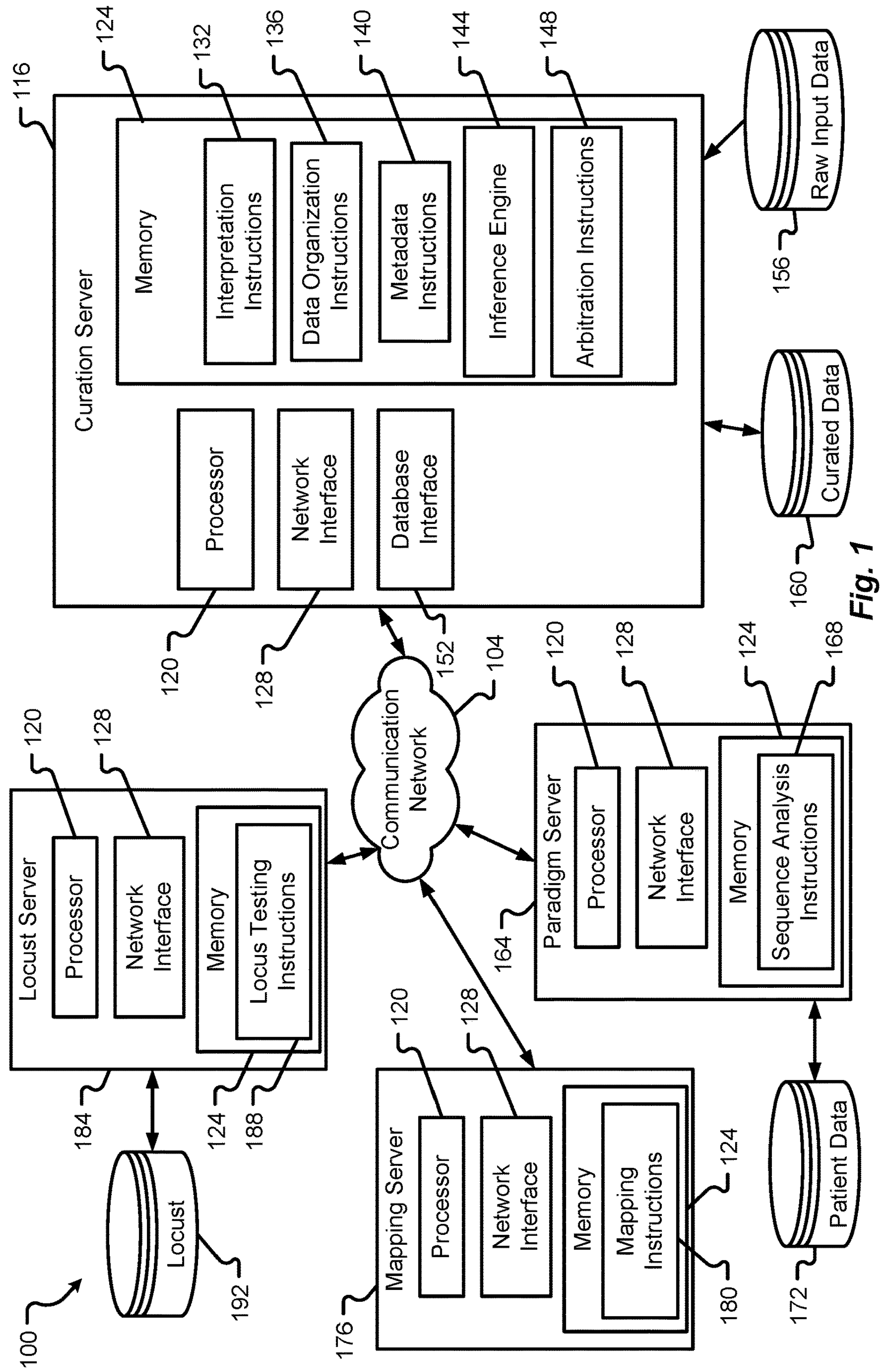
FIG. 1 is a block diagram depicting a system in accordance with at least some embodiments of the present disclosure.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

One should appreciate that the disclosed techniques provide many advantageous technical effects including the ability to analyze vast quantities of data in a limited amount of time and with less processing power than was previously required, by analyzing sequence fragments and k-mers therein rather than entire sequences; the ability to call variants that are hard to call with usual methods; the ability to complete variant calling of DNA or RNA sequences without use of RefSeq transcripts, a reference genome, or other additional information; the ability to detect, with a portable database containing all information necessary for calling, single nucleotide variants, small insertions and/or deletions, multiple nucleotide variants, large insertions and/or deletions, mitochondrial haplogroups, and gene fusions.

The focus of the disclosed inventive subject matter is to enable construction or configuration of a computing device to operate on vast quantities of digital data, beyond the capabilities of a human. Although the digital data represent DNA or RNA sequences and their variants, it should be appreciated that the digital data are a representation of one or more digital models of DNA or RNA sequences and their variants, not DNA or RNA sequences and their variants themselves. By instantiation of such digital models in the memory of the computing devices, the computing devices are able to manage the digital data or models in a manner that could provide utility to a user of the computing device that the user would lack without such a tool.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting.

Figure 2:
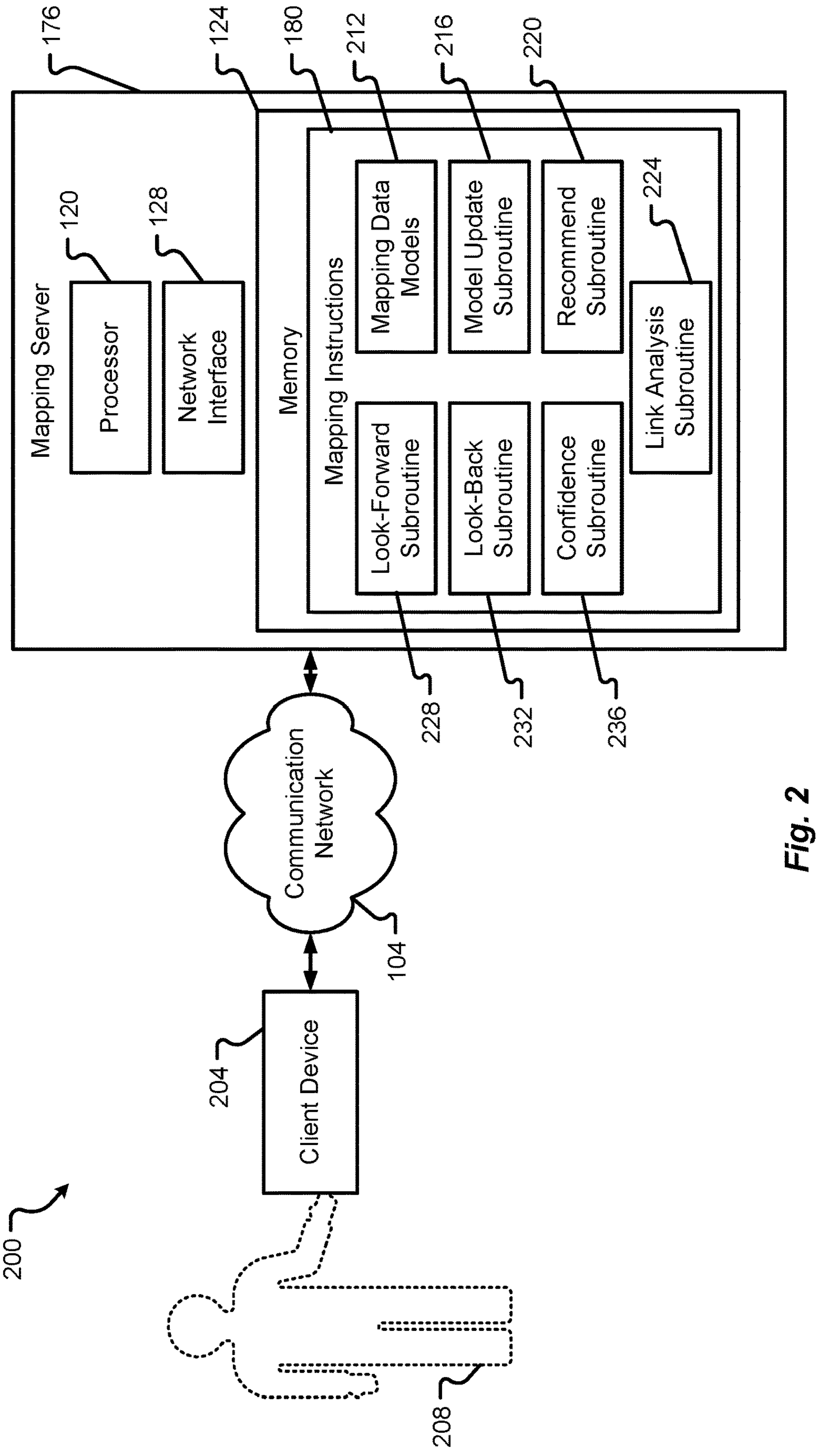
FIG. 2 is a block diagram depicting additional details of a system in accordance with at least some embodiments of the present disclosure.
Figure 3:
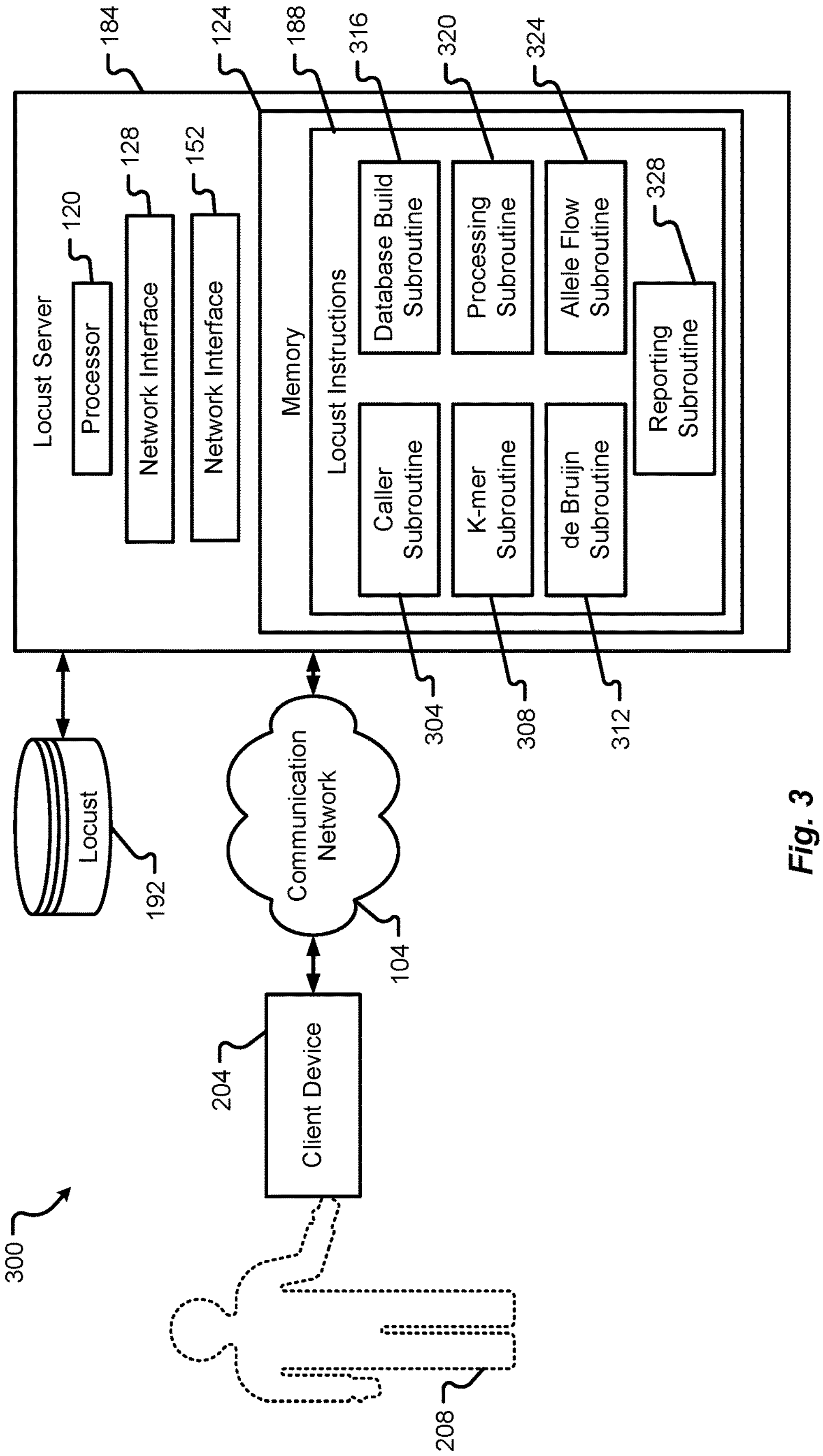
FIG. 3 is a block diagram depicting further details of a system in accordance with at least some embodiments of the present disclosure.

With reference to FIGS. 1-3, illustrative systems 100, 200, 300 will be described in accordance with at least some embodiments of the present disclosure. The systems 100, 200, 300 in some embodiments, may include one or more computing devices operating in cooperation with one another to provide data curation and mapping functions. The components of the systems 100, 200, 300 may be utilized to facilitate one, some, or all of the methods described herein or portions thereof without departing from the scope of the present disclosure. Furthermore, although particular servers are depicted as including particular components or instruction sets, it should be appreciated that embodiments of the present disclosure are not so limited. For instance, a single server may be provided with all of the instruction sets depicted and described in the servers of FIGS. 1-3. Alternatively, different servers may be provided with different instruction sets than those depicted in FIGS. 1-3.

The systems 100, 200, 300 are shown to include a communication network 104 that facilitates machine-to-machine communications between one or more servers 116, 164, 176, 184 and/or one or more client devices 204. The system 100 is shown to include a curation server 116, a paradigm (pathway recognition algorithm using data integration on genomic models) server 164, a mapping server 176, and a locust (locus tester) server 184. The system 200 shows additional details of the mapping server 176, and the system 300 shows additional details of the locust server 184.

The communication network 104 may comprise any type of known communication medium or collection of communication media and may use any type of protocols to transport messages between endpoints. The communication network 104 may include wired and/or wireless communication technologies. The Internet is an example of the communication network 104 that constitutes an Internet Protocol (IP) network consisting of many computers, computing networks, and other communication devices located all over the world, which are connected through many telephone systems and other means. Other examples of the communication network 104 include, without limitation, a standard Plain Old Telephone System (POTS), an Integrated Services Digital Network (ISDN), the Public Switched Telephone Network (PSTN), a Local Area Network (LAN), a Wide Area Network (WAN), a Session Initiation Protocol (SIP) network, a Voice over Internet Protocol (VoIP) network, a cellular network, and any other type of packet-switched or circuit-switched network known in the art. In addition, it can be appreciated that the communication network 104 need not be limited to any one network type, and instead may be comprised of a number of different networks and/or network types. Moreover, the communication network 104 may comprise a number of different communication media such as coaxial cable, copper cable/wire, fiber-optic cable, antennas for transmitting/receiving wireless messages, and combinations thereof.

The client device 204 may correspond to any type of computing resource that includes a processor, computer memory, and a user interface. The client device 204 may also include one or more network interfaces that connect the client device 204 to the communication network 104 and enable the client device 204 to send/receive packets via the communication network 104. Non-limiting examples of client devices 204 include personal computers, laptops, mobile phones, smart phones, tablets, etc. In some embodiments, the client device 204 is configured to be used by and/or carried by a user 208. As will be discussed in further detail herein, the user 208 may utilize a client device 204 to receive and/or view various outputs of the servers 116, 164, 176, 184.

The servers 116, 164, 176, 184 or components thereof may be provided as a single server or in a cloud-computing environment. The curation server 116 may be configured to execute one or multiple different types of instruction sets in connection with processing biological process data received from a biological process input data source 156 and transforming the biological process data into curated data 160 that is useable by the paradigm server 164, the mapping server 176, and/or the locust server 184. As will be discussed in further detail herein, the biological process input data received from the biological process input data source 156 may include data relating to (i) the identity of a biological or chemical entity; (ii) the function of a biological or chemical entity; or (iii) the relationship between the function of a biological or chemical entity and another biological or chemical entity. The biological process input data may alternatively, or additionally, include other types of biological data. As will be discussed in further detail herein, the curation server 116 may be configured to process the biological process input data into a normalized (or flattened) data space in which the paradigm server 164, the mapping server 176, and/or the locust server 184 are configured to process data. In this way, the curation server 116 helps condition the biological process input data into data that comprises a digestible format for the other servers 164, 176, 184.

Biological process input data related to a biological or chemical entity can refer to genes; nucleic acid molecules (DNA or RNA), including sequence information; proteins, including amino acid sequence information and/or three-dimensional structure and/or post-translational modifications; organelles; cells; organs; and organisms. Biological process input data can include information regarding different states of a biological or chemical entity, for example, information regarding an unmodified protein as compared to phosphorylated protein or a free base form of a drug as compared to a salt of the drug. Biological process input data can also include any "omics" data, including genomics, transcriptomics, proteomics or metabolomics.

The curation server 116 is shown to include a processor 120, memory 124, and network interface 128. The curation server 116 is also shown to include a database interface 152, which may be provided as a physical set of database links and drivers. Alternatively or additionally, the database interface may be provided as one or more instruction sets in memory 124 that enable the processor 120 of the curation server 116 to interact with the databases 156, 160.

These resources of the curation server 116 may enable functionality of the curation server 116 as will be described herein. The network interface 128 provides the server 116 with the ability to send and receive communication packets over the communication network 104. The network interface 128 may be provided as a network interface card (NIC), a network port, drivers for the same, and the like. Communications between the components of the server 116 and other devices connected to the communication network 104 may all flow through the network interface 128.

The processor 120 may correspond to one or many computer processing devices. For instance, the processor 120 may be provided as silicon, as a Field Programmable Gate Array (FPGA), an Application-Specific Integrated Circuit (ASIC), any other type of Integrated Circuit (IC) chip, a collection of IC chips, or the like. As a more specific example, the processor 120 may be provided as a microprocessor, Central Processing Unit (CPU), or plurality of microprocessors that are configured to execute the instructions sets stored in memory 124. Upon executing the instruction sets stored in memory 124, the processor 120 enables various functions of the curation server 116.

The memory 124 may include any type of computer memory device or collection of computer memory devices. Non-limiting examples of memory 124 include Random Access Memory (RAM), Read Only Memory (ROM), flash memory, Electronically-Erasable Programmable ROM (EEPROM), Dynamic RAM (DRAM), etc. The memory 124 may be configured to store the instruction sets depicted in addition to temporarily storing data for the processor 120 to execute various types of routines or functions. Although not depicted, the memory 124 may include instructions that enable the processor 120 to store or retrieve data from the databases 156, 160. Further still, the memory 124 may include instructions that enable the curation server 116 to provide curated data from the curated database 160 to the paradigm server 164, the mapping server 176, and/or the locust server 184 for additional processing.

The illustrative instruction sets that may be stored in memory 124 include, without limitation, interpretation instructions 132, data organization instructions 136, metadata instructions 140, an inference engine 144, and arbitration instructions 148. In some embodiments, the interpretation instructions 124, when processed by the processor 120, enable the curation server 116 to scan and analyze the biological process input data received from the biological process input data source 156 and identify one or more topics, conclusions, recurring words, semantic topics, etc. For example, in the instance of an item (i.e., a datum) of biological process input data being an active pharmaceutical ingredient (API), the curation server 116 may access a data source comprising characteristics or information about the API, such as structural analogs, cell receptor binding partners, metabolic pathways affected by the API, etc. In some embodiments, the interpretation instructions 132 enable the curation server 116 to index the biological process input data and to further assign appropriate tags to the biological process input data. As a specific, but non-limiting example, the biological process input data may correspond to research papers, review papers, research posters, medical publications, clinical trial reports, white papers, or Food and Drug Administration (FDA) or other governing health bodies/agencies reports. Thus, in some embodiments, the biological process input data correspond to textual data, which may be focused on a particular topic and which may provide one or more conclusions. The interpretation instructions 132 may be configured to automatically scan the text of the biological process input data and extract the topic(s) discussed, the data analyzed, and/or the conclusions drawn within the biological process input data.

The data organization instructions 136 may be configured to organize the data output by the interpretation instructions 132 for eventual storage as curated data within the curated database 160. For instance, the data organization instructions 136 may enable the server 116 to organize the biological process input data based on the complex data outputs of the interpretation instructions 132 and/or based on inferences drawn by the inference engine 144. In some embodiments, the data organization instructions 136 not only organize the biological process input data and index the data based on the organization, but the organization instructions 136 also enable the server 116 to normalize the data to the central dogma of molecular biology. In some embodiments, the data organization instructions 136 may be configured to organize the various data inputs based on a genomics organizational structure. A non-limiting example of a genomics organization structure includes, without limitation, shared/common pathways, cell communication behaviors, and/or cellular network behaviors.

The metadata instructions 140 may be configured to extract metadata from the biological process input data if such metadata already existed within the biological process input data, create additional metadata based on outputs of the data organization instructions 136, and possibly provide inputs to the data organization instructions 136 to assist with the organization of data based, at least in part, on the metadata associated with the biological process input data. In some embodiments, the metadata instructions are configured to generate metadata for the biological process input data that will ultimately match a format of metadata from patient-specific data within the central dogma. Thus, if any metadata will be extracted from or associated with patient-specific data, then corresponding metadata may be extracted from or generated based on the biological process input data. As a non-limiting example, metadata that can be associated with curated data may include patient gender, patient age, article/biological process input data age, article/biological process input data publication date, article/biological process input data author(s) or authorities, treatment information, drug information, combinations thereof, keywords, and the like. Any type of information related to an article or similar type of biological process input data may be formatted into metadata by the metadata instructions 140.

The inference engine 144, when executed by the processor 120, may enable the server 116 to analyze the biological process input data or curated data to search for inferences that can be made based on the data structure. In some embodiments, the inference engine 144 may be configured to make inferences of drug/treatment efficacy, side-effects, or possibly alternative (yet to be reported) drug/treatment effects. More specifically, the inference engine 144 may be configured to analyze the biological process input data or curated data and generate one or more inferences based on some known biological features from the data and then generate an inference for unknown features to extend one or more known biological features or characteristics. These features can then be mapped to the curated data and, possibly, verified for final mapping or association with the curated data. In some embodiments, an inference may be automatically mapped to or associated with curated data in the event that the inference is made with at least a predetermined confidence score (e.g., a confidence score that meets or exceeds a predetermined threshold). In some embodiments, an inference may require a manual review prior to being mapped to or associated with curated data. For instance, details of the inference generated by the inference engine 144 may be provided to a predetermined user (e.g., a medical professional, a medical researcher, a governmental entity, etc.) for review and approval.

The arbitration instructions 148 may be configured to resolve conflicts between inference rules generated by the inference engine 144 and/or between conclusions drawn between curated data within the database 160. In some embodiments, the arbitration instructions 148 may also enable the curation server 116 to adhere to a predetermined policy or philosophy in connection with resolving such inference conflicts. In some embodiments, these predetermined policies or philosophies may be applied to newly-generated inferences as well as inferences that were previously generated by the inference engine 144 and stored in connection with curated data.

Although not depicted, but as will be described in further detail herein, the curation server 116 may also have one or more of its instruction sets (e.g., the inference engine 144) executed as a neural network or similar type of artificial intelligence data structure. Furthermore, these neural networks, such as an intelligent inference engine 144, may be capable of being dynamically trained and updated based on outputs of the curation server 116, based on outputs of the mapping server 176, the paradigm server 164, and/or the locust server 184. Further still, one or more models used by an intelligent inference engine 144 may be constantly analyzed for possible improvements thereto. Such analysis may be done internally or by an external neural network that is specifically designed to train other neural networks. As another non-limiting example, the data organization instructions 136 may be executed as a neural network whose coefficients between nodes are constantly updated in accordance with desired updates to the data organization for the curated data. For instance, if a particular normalized data space is initially used by the data organization instructions 136, but there is a desire to try a second, different, normalized data space that focuses on different biological information (e.g., shared pathways as compared to cellular communication behaviors), then the data organization instructions 136 may be reconfigured (e.g., offline rather than reconfiguring online with live data) to determine if using a different normalized data space is useful, provides certain benefits, or makes the overall system work less efficiently. If it is determined that the different normalized data space provides an improvement over the original normalized data space, then the data organization instructions 136 may be updated within the curation server 116 to begin applying the new normalized data space to further organizations of the curated data.

The paradigm server 164 is shown to include several components that are similar or identical to the curation server 116. For instance, the paradigm server 164 may include one or more processors 120, a network interface 128, and memory 124. Although not depicted, the paradigm server 164 may be provided with a database interface 152 to facilitate interactions with a database 172 that stores patient-specific data. In some embodiments, the paradigm server 164 is provided with sequence analysis instructions 168 that, when executed by the processor 120, enable the paradigm server 164 to receive and analyze patient-specific data from the database 172. In a more specific but non-limiting example, the sequence analysis instructions 168 may enable the paradigm server 164 to characterize individual patient tumors and to select therapies based on the identified mutations. Thus, the paradigm server 164 may be configured to perform matched tumor-normal sequencing analyses to assist in the precise identification and interpretation of somatic and/or germline alterations within a patient's genomic data set. In some embodiments, the sequence analysis instructions 168 may also enable the server 164 to format the patient-specific data from the database 172 based on the central dogma, consistent with a normalized data organization used for the curated data in the curated database 160. In some embodiments, the paradigm server 164 is configured to receive patient-specific data in the form of one or more of gene expression data from an RNA sequence, CNV profiles from a DNA sequence, protein abundance data from a protein data set, etc. and then to prepare one or more interaction pathway data sets that are comparable to the curated data. As an example, pathway activity levels may be comparable to the curated data or a subset thereof within the mapping server 176. For example, methods for using pathway recognition algorithms using data integration on genomic models are disclosed in, for example, U.S. Patent Publication 2012/0041683.

The mapping server 176 is also shown to include a processor 120, memory 124, and network interface 128. In some embodiments, the memory 124 of the mapping server 176 may be provided with mapping instructions 180 that, when executed by the processor 120, enable the mapping server 176 to map patient-specific data received from the paradigm server 164 with curated data from the curation server 116. In some embodiments, the mapping instructions 180 may include a set of data call instructions that enable the mapping server 176 to call or request instances or discrete sets of patient-specific data from the paradigm server 164 and call or request related curated data from the curation server 116. The mapping instructions 180 may also receive genomic data from one or both of the paradigm server 164 and curation server 116 and produce a responder vs. no responder determination from the curated data.

The locust server 184 is also shown to include a processor 120, memory 124, and network interface 128. In some embodiments, the memory 124 of the locust server 184 may be provided with locus testing instructions 188 that, when executed by the processor 120, enable the locust server 184 to build the locust database 192 using data received from one or more of the databases 156 and 160 (via the curation server 116) and the database 172 (via the paradigm server 164). In some embodiments, the locus testing instructions 188 may include a set of data call instructions that enable the locust server 184 to call or request instances or discrete sets of data from the paradigm server 164 and call or request related curated data from the curation server 116. Also in some embodiments, the locus testing instructions 188 may include a set of data call instructions that enable the locust server 184 to call or request instances or discrete sets of data from the locust database 192. The locust instructions 188 may also include a set of instructions for analyzing data in the locust database 192 and/or for updating the locust database 192. The locust server may comprise a database interface, which may be the same as or similar to the database interface 152, and which may facilitate interaction of the locust server 184 with the database 192.

As shown in FIG. 2, the mapping instructions 180 may be provided with a number of subroutines that further enable the functionality of the mapping instructions 180. While the mapping instructions 180 and its subroutines are shown as being provided within the mapping server 176, it should be appreciated that the mapping instructions 180 or subroutines thereof may be provided in the curation server 116, the paradigm server 164, and/or the locust server 184 without departing from the scope of the present disclosure. Non-limiting examples of subroutines that may be incorporated within the mapping instructions 180 include mapping data models 212, a model update subroutine 216, a recommendation subroutine 220, a link analysis subroutine 224, a look-forward subroutine 228, a look-back subroutine 232, and a confidence subroutine 236.

The mapping data models 212 may include one or more neural networks or similarly-constructed data-based computer learning models that receive curated data as well as patient-specific data as an input and provide one or more outputs describing a relationship between the curated data and patient-specific data. The mapping data models 212 may be statically defined or may be updated, from time-to-time, with the assistance of the model update subroutine 216. The model update subroutine 216 may be configured to analyze outputs of the mapping data models 212 and determine whether such outputs have been determined an accurate match, a mismatch, a false positive, etc. This information may be used by the model update subroutine 216 to determine whether any coefficients within the mapping data models 212 should be updated or whether the models themselves should be updated to achieve a higher accuracy of match between patient-specific data and curated data.

The recommendation subroutine 220 may be provided to generate and send one or more recommendations for treatment to a healthcare provider based on a mapping outcome provided by the mapping data models 212. For instance, the mapping data models 212 may indicate that one or more patient-specific data sets are closely related to one or more curated data sets. Information from the curated data set that closely relates to the patient-specific data set may be used to prepare one or more recommendations for treatment to the patient. The recommendation subroutine 220 may even utilize one or more of the link analysis subroutine 224, look-forward subroutine, look-back subroutine 232, and confidence subroutine 236 to assist with the creation of such recommendations and scoring of such recommendations. For instance, the link analysis subroutine 224 can be used to search across pathway interconnects based on known tumor types and known treatments having known outcomes and infer relationships for other tumor types that exhibit similar link behaviors. Pathway interactions can also be used by the look-forward subroutine 228 and look-back subroutine 232 to help determine whether any matches exist between inference structures in the curated data and the patient-specific data. Because the curated data may be formatted based on the central dogma consistent with a format of the patient-specific data, the matching processing performed by the link analysis subroutine 224, with the assistance of the look-forward 228 and look-back subroutines 232 can be performed relatively quickly and efficiently.

The confidence subroutine 246 may enable the mapping instructions 180 to determine a confidence score or index associated with each inference generated by the link analysis subroutine 224 and/or recommendations provided by the recommendation subroutine 220. Such confidence scores may be based on a number of data sources used to generate an inference or recommendation, a degree of proximity between a patient-specific data instance and a curated data instance, a degree of proximity between a patient-specific data instance and data contained in the mapping data models 212, a number of conflicts identified between inferences (e.g., to decrease a particular confidence score), and so on. If a confidence score for a particular inference or recommendation is not at or above a predetermined threshold, then a user 208 may be notified of the deficiency or provided with the actual confidence score to let the user 208 know that an inference or recommendation is not provided with a full level of confidence. As more data are fed into the mapping data models 212, the overall confidence levels may improve or a threshold required for automated functions may increase.

As shown in FIG. 3, the locust instructions 188 may be provided with a number of subroutines that further enable the functionality of the locust instructions 180. While the locust instructions 188 and associated subroutines are shown as being provided within the locust server 184, it should be appreciated that the locust instructions 188 or subroutines thereof may be provided in the curation server 116, the paradigm server 164, and/or the mapping server 176 without departing from the scope of the present disclosure. Non-limiting examples of subroutines that may be incorporated within the locust instructions 188 include a caller subroutine 304, a k-mer subroutine 308, a de Bruijn subroutine 312, a database build subroutine 316, a processing subroutine 320, an allele flow subroutine 324, and a reporting subroutine 328.

The caller subroutine 304 may comprise instructions for calling one or more DNA or RNA sequences from, for example, the databases 156, 160, and/or 172. In some embodiments, the caller subroutine 304 may also comprise instructions for calling one or more DNA or RNA sequences from the database 192. Also in some embodiments, the caller subroutine 304 may be configured to extract relevant reads from a genomic location in indexed Binary Alignment Maps or BAMs (which indexed BAMs may be stored in any of the databases 156, 160, and/or 172). The caller subroutine 304 may enable precise control over what sequence variants are callable, and may be configured to ignore read alignments from BWA or other aligners. Beneficially, the caller subroutine 304 may enable the calling of a one or more DNA or RNA sequences or sequence variants without needing additional information such as RefSeq transcripts, a reference genome, etc. for analysis or annotation. Also, the caller subroutine 304 may be able to call DNA or RNA sequences or sequence variants from data stores in the cloud, without first needing to download the data store or data therefrom. The caller subroutine 304 may be used, for example, to call known or recurrent somatic mutations in key genes, such as KRAS, TPF3, etc.; to call pathogenic or likely pathogenic germline variants, such as BRCA1, BRCA2; and/or to call variants that are hard to call with usual methods, such as TYMS VNTR region, BRCA2 c.156_157insAlu.

The k-mer subroutine 308 may configured to identify the k-mers in a given DNA or RNA sequence, where k can be any integer from 2 to at least 65. Each k-mer may be in the format "<Previous Base>-Edge-<Next Base>. For example, the sequence "ATTAGC" has the following k-mers for k=2: A-TT-A, T-TA-G, T-AG-C. As another example, the same sequence has the following k-mers for k=3: A-TTA-G, T-TAG-C. The <Previous Base> and <Next Base> can encode local duplicate structure. For example, the sequence CATTTTTTCG (SEQ ID NO: 13) has the following k-mers for k=2: C-AT-T, A-TT-T, T-TT-T, T-TT-T, T-TT-T, T-TT-C, T-TC-G. K-mers with shared edges may be collapsed into a single representative k-mer; for example, the foregoing k-mers for the sequence CATTTTTTCG (SEQ ID NO: 13) may be reduced to C-AT-T, ATTTT-TT-TTTTC, T-TC-G.

Figure 5:
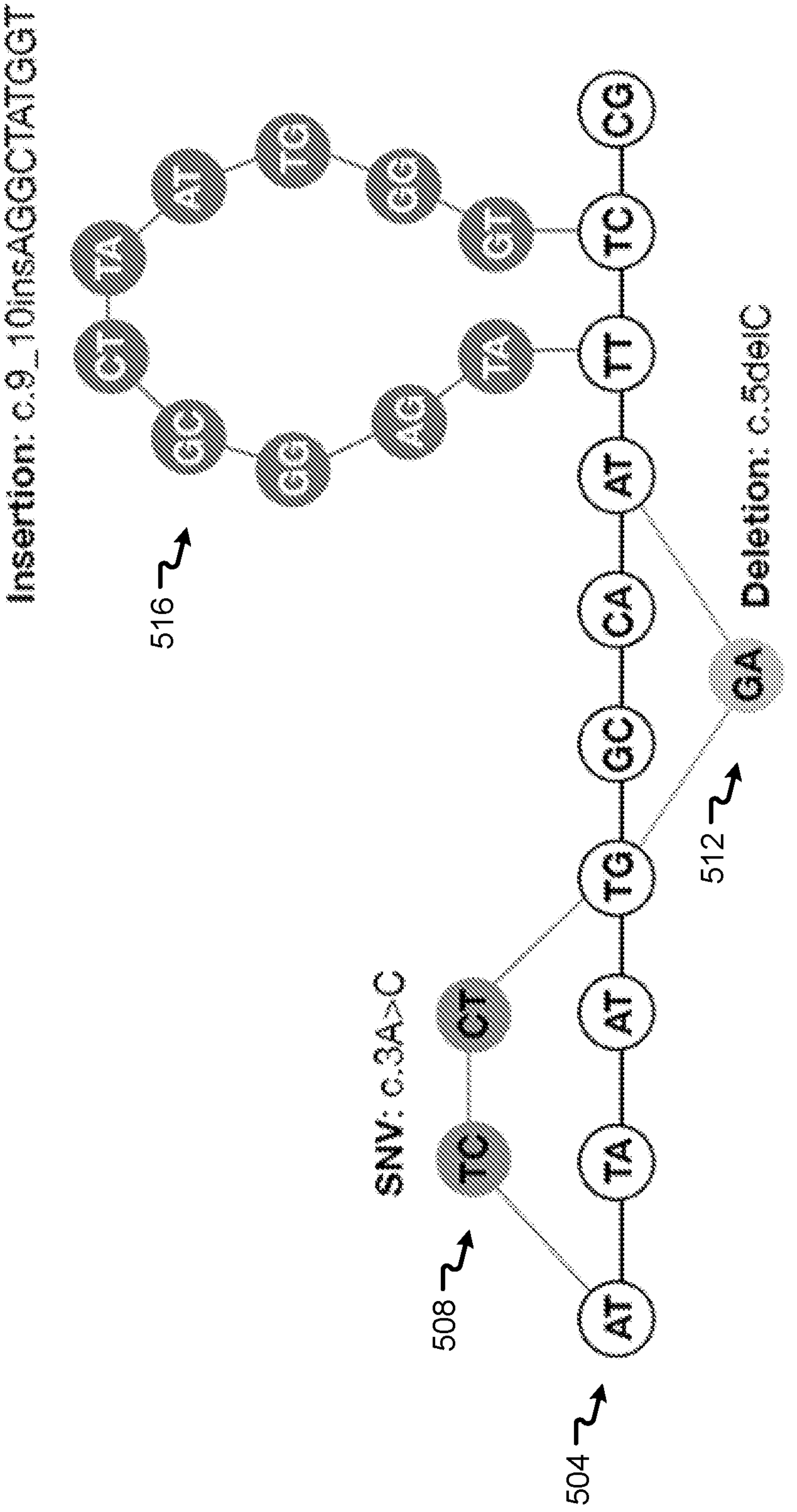
FIG. 5 is a graphical depiction of DNA or RNA sequence data at a locus of interest in accordance with at least some embodiments of the present disclosure (wherein AGGCTATGGT is SEQ ID NO:18)

The de Bruijn subroutine 312 may comprise instructions for generating a de Bruijn graph (or equivalent thereof, including an expression thereof in software code or text) of a DNA or RNA sequence and the variants thereof, using k-mers of the sequence in question and the variants thereof. Thus, for example and with respect to FIG. 5, the de Bruijn graph (or equivalent thereof) may contain the k-mer edges 504 of a given sequence (e.g., AT, TA, AT, etc. for the sequence ATATGCATTCG (SEQ ID NO: 14)); any k-mer edges 508 that are changed by a single nucleotide variant of the sequence (e.g., TC, CT for the sequence ATCTGCATTCG (SEQ ID NO: 15), in which the third nucleotide in the original sequence has been changed from A to C); any k-mer edges 512 that are changed by a deletion in the original sequence (e.g., GA for the sequence ATATG-ATTCG, in which the sixth nucleotide C has been deleted from the original sequence); and any k-mer edges 516 that are added by an insertion in the original sequence (e.g., TA, AG, GG, GC, CT, etc. in the sequence ATATGCATTAGGCTATGGTCG (SEQ ID NO: 17), in which the new sequence AGGCTATGGT (SEQ ID NO: 18) has been inserted before the final two nucleotides in the original sequence). A textual representation of the de Bruijn graph may utilize shorthand to describe variants of the original sequence, such as c.3A>C to describe the single nucleotide variant of the sequence described above; c.6delC to describe the variant of the sequence described above in which a nucleotide has been deleted; and c.9_10insAGGCTATGGT (wherein AGGCTATGGT is SEQ ID NO:18) to describe the variant of the sequence described above in which the AGGCTATGGT (SEQ ID NO:18) sequence has been inserted into the original sequence.

Figure 6:
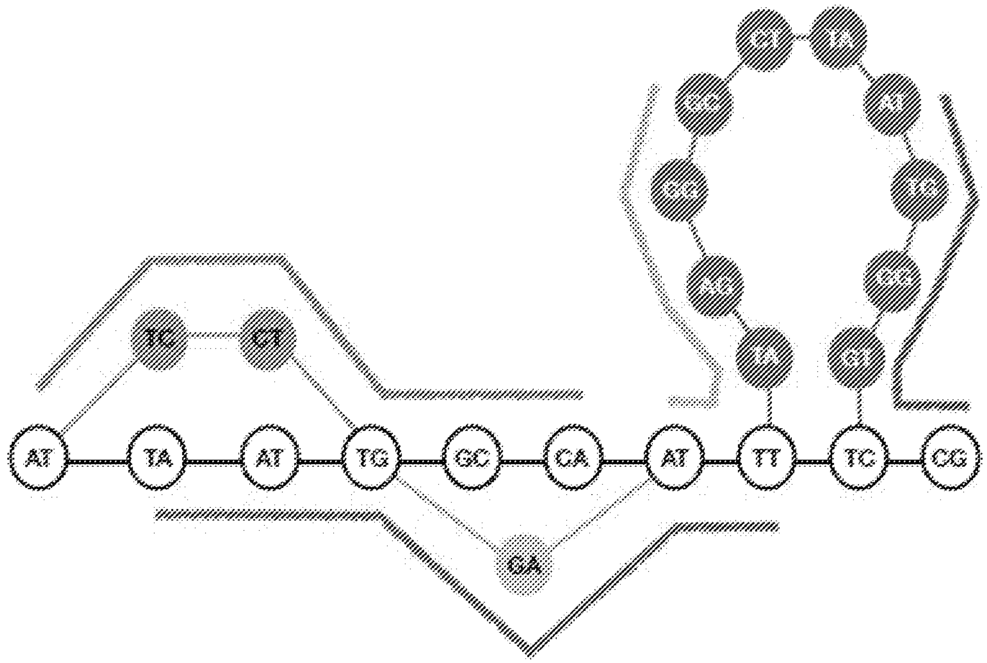
FIG. 6 illustrates the preparation of a locust database comprising k-mers and tags thereof in accordance with at least some embodiments of the present disclosure (wherein AGGCTATGGT is SEQ ID NO:18)

The database build subroutine 316 may generate a database using a de Bruijn graph or equivalent thereof generated by the de Bruijn subroutine 312, as shown in FIG. 6. More specifically, the database build subroutine 316 may comprise a list of all k-mers from the de Bruijn graph (or equivalent thereof), and may tag each k-mer depending on whether the k-mer corresponds to the original sequence or a variant thereof. Thus, for example, the k-mers A-TA-T, T-AT-G, and A-TG-C-all of which appear in the original sequence—may be tagged or otherwise identified as "reference" or "ref" k-mers. The k-mers A-TC-C and T-CT-G—which appear in the single nucleotide variant of the original sequence, in which the third nucleotide has been changed from A to C—may be tagged or otherwise identified with a shorthand describing the variant in question (e.g., c.3A>C). The k-mers A-TG-A and T-GA-T—which appear in the variant of the original sequence in which the sixth nucleotide C has been deleted—may be also tagged or otherwise identified with a corresponding shorthand (e.g., c.6delC). Similarly, the k-mers C-AT-T, A-TT-A, T-TA-G, T-AG-G, A-GG-C, A-TG-G, T-GG-T—which appear (along with other k-mers) in the variant in which the new sequence AGGCTATGGT (SEQ ID NO:18) has been inserted—may be tagged with a corresponding shorthand (e.g., c.9_10insAGGCTATGGT wherein AGGCTATGGT is SEQ ID NO:18). Thus, the database build subroutine 316 assembles a database that identifies, for a given sequence of DNA or RNA, the k-mers in both the sequence itself as well as in variants of the sequence. The assembled database may be, for example, the locust database 192.

The locust database 192 may be generated from, for example, biomarkers in the curation database 160, and/or from a user-inputted list of variants of interest, and/or from the ClinVar database search. In some embodiments, the locust database 192 may be structured as a relational database, and may capture the relationships between and among locusts, patients, k-mers, variants, and results. As shown in FIG. 7, for example, the locust database 192 may comprise relational tables for variant ID and locust ID; locust ID, region, and k-mer length; patient ID, tumor type, and age; variant ID and k-mer; variant ID, gene, coding change, and protein change; and/or variant ID, patient ID, and variant allele flow. The locust database 192 may be focused on actionable mutations in an oncogenic panel of genes, such as recurrent somatic variants, known/likely pathogenic germline variants (incidental/secondary findings), and fusions (303 panel).

Figure 8:
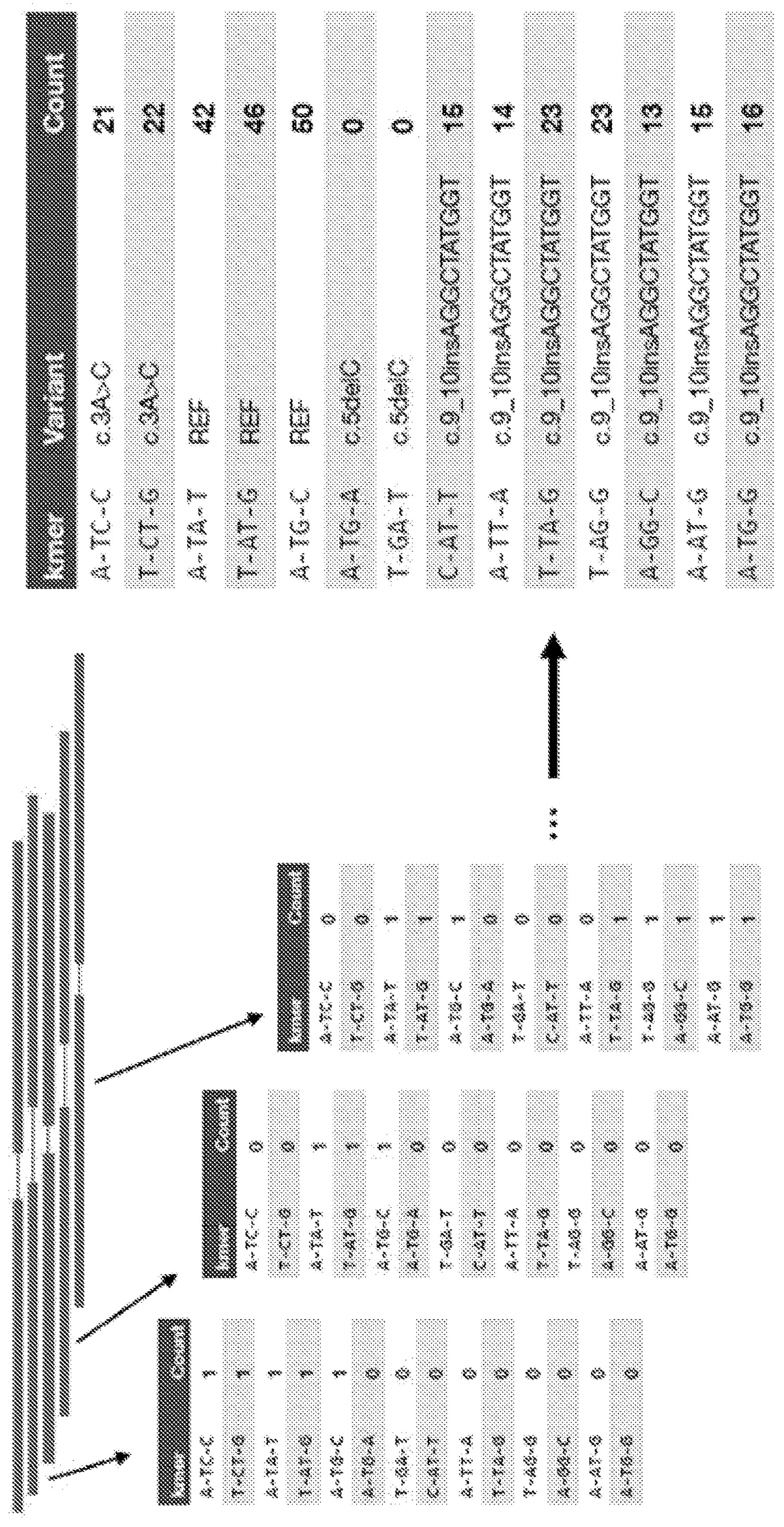
FIG. 8 illustrates the determination of k-mer counts for inclusion in a locust database in accordance with at least some embodiments of the present disclosure (wherein AGGCTATGGT is SEQ ID NO:18)

As shown in FIG. 8, the processing subroutine 320 processes paired reads (e.g., reads of the same k-mer sequence from the same genomic location in different sets of data) as fragments, and counts the number of times each k-mer (including k-mers in the original sequence and k-mers in the variant sequences) appears. For example, the k-mer A-TA-T may appear in each of 42 reads, but the k-mer A-TT-A may appear in only 14 of 42 reads. The k-mer count for each k-mer may be added to the database 192 or other database resulting from execution of the database build subroutine 316. In some embodiments, an identified k-mer that does not appear in any read, or that appears only in statistically insignificant number of reads, may be removed from the database. This should only occur with variant k-mers, as reference k-mers should appear in every non-variant instance of a given sequence.

Figure 9:
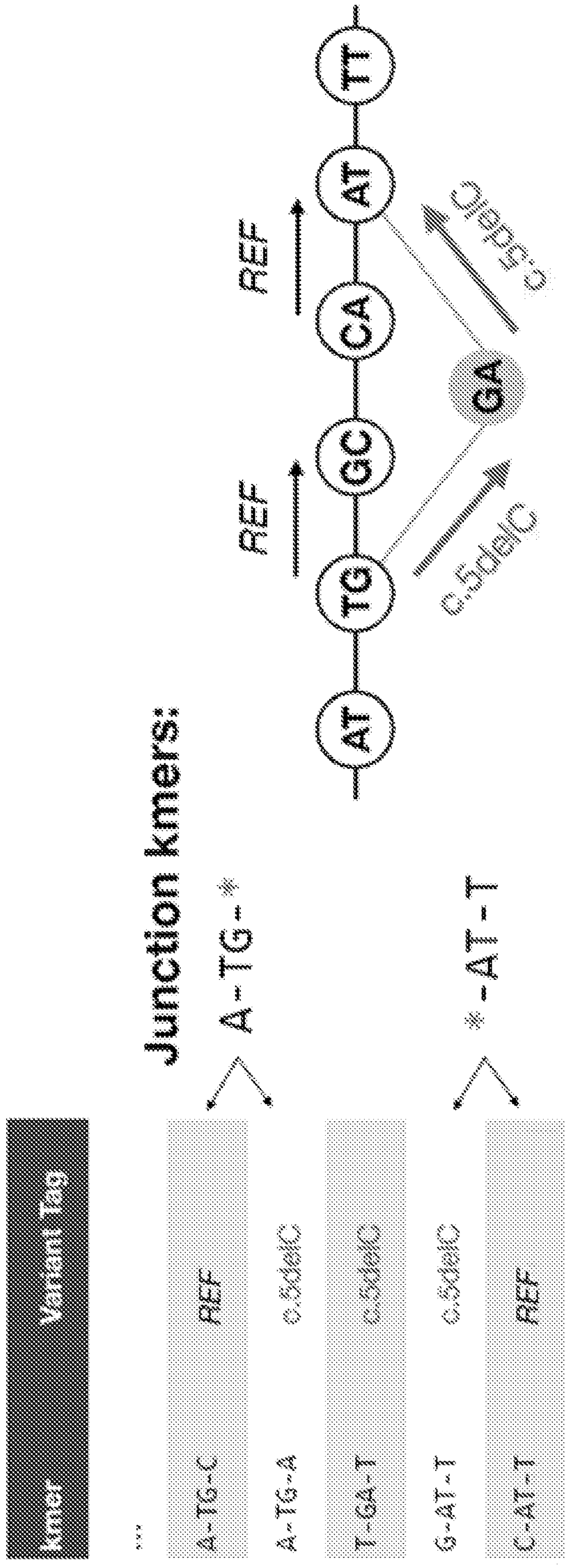
FIG. 9 illustrates the concept of junction k-mers in accordance with at least some embodiments of the present disclosure.

As used herein, reference to "allele flow" is relative measurement of how many sequencing data flow across a variant's edges, i.e., it is a measure of the relative frequency of a variant in a data set. For example, allele flow can be calculated as the relative occurrence of an allele in a population, such as (variant/(reference+variant). The allele flow subroutine 324 identifies junction k-mers (as shown in FIG. 9) and calculates the relative support at these junctions. Junction k-mers are k-mers at the junction where a modification to a given sequence begins or ends, and therefore that either (1) share a <Previous Base> and Edge, but have a <Next Base> that varies depending on whether the sequence in question is a variant or not, or (2) share an Edge and <Next Base>, but have a <Previous Base> that varies depending on whether the sequence in question is a variant or not. Junction k-mers are especially noticeable on a de Bruijn graph, as the Edge of a junction k-mer is connected to a plurality of <Next Bases> or to a plurality of <Previous Bases>. By of example, an original sequence ATGCATT may have a deletion variant ATGATT. The k-mers A-TG-C (from the original sequence) and A-TG-A (from the variant sequence) are junction k-mers: they provide an indication of whether or not the sequence in question matches the original sequence or the deletion variant thereof. The <Next Base> of these k-mers varies depending on whether the sequence being read is an original sequence (in which case the <Next Base is C) or a variant sequence (in which case the <Next Base> is A). Similar, the k-mers G-AT-T (from the original sequence) and C-AT-T (from the variant sequence) are also junction k-mers. The share the same Edge and <Next Base>, but have a different <Previous Base> depending on whether the sequence in question matches the original sequence or is a variant sequence.

The allele flow subroutine 324 calculates the relative support at k-mer junctions by dividing the counted number of appearances of the variant junction k-mer by the sum of the counted number of appearances of the variant junction k-mer and the reference junction k-mer. Thus, for example, if the counted number of appearances of the variant junction k-mer is 14, and the counted number of appearances of the original junction k-mer is 28, then the relative support would be 14/(14+28)=33%. The relative support is an indication of how many sequencing data flow across the variant's edges. The relative support may also be understood as an indication of how frequently a given variant occurs.

The reporting subroutine 328 generates reports based on information contained in the locust database 192. In some embodiments, the reporting subroutine 328 may generate a custom curated report based on BAMs and data in the locust database 192. The reporting subroutine 328 may run the report immediately post-alignment, thereby bypassing other analyses of genetic information, such as GPS Cancer™ (offered by NantHealth). The locust database 192 may store additional structured data for reporting, for example, drug associations (including, e.g., sensitivity and response); a clinical significance (e.g., pathogenic, likely pathogenic) from ClinVar; COSMIC prevalence; Population Allele Frequencies for germline variants; and the like. In some embodiments, the reporting subroutine 328 may utilized RNA express analyses to augment reporting, such as tissue site prediction, CMS subtyper, hormone receptor status (ER/PR/Her2), PAM50 subtyper, immune panel express, chemo response panel, and viral gene expression.

The systems and methods described herein, including the locust server 184 and the locust database 192, may be used to detect small changes in DNA or RNA sequences (such as single nucleotide variations, small insertions or deletions, multi-nucleotide variations, and/or subs or delins), big changes in DNA or RNA sequences (such as large deletions, mitochondrial haplogroups), RNA-specific variations (such as gene fusions), and less common variations (such as BRCA Alu insertions, TYMS VNTR genotypes). Alignments do not affect the operation thereof, and whether the analyzed sequence originated in DNA or RNA is immaterial. The database 192 may be portable and may contain all information necessary for calling.

In some embodiments, a locust database 192 may be stored in a queryable database such as MongoDB or the like. Also in some embodiments, rapid updating of the set of discoverable variants stored in the database 192 is possible. A locust pipeline may be configured to query a database (with arguments such as "gene" or "BRCA1") to generate a local JSON database that may then be used for processing.

In some embodiments, all possible single nucleotide variants within gene hotspots, whether previously observed or not, may be added to the locust database 192. The locust database 192 may be searchable for all possible coding changes (single nucleotide variants, insertions, deletions, etc.) that cause protein change. Common germline single nucleotide polymorphisms (SNPs) may be combined with single nucleotide variations in the database 192 to generate 'phased' graphlets whenever the SNP is within a k-mer's distance of the single nucleotide variation. A patient's sequencing data surrounding a novel variant may be used to augment the locust database 192.

In some embodiments, when unmatched k-mers are found in input data, the sample in which the unmatched k-mers are found may be flagged for novel variant discovery. In some embodiments, GPS Cancer™ may be used in connection with this process. The locust database 192 may be updated with the novel variant so that the variant may be reported in the future.

The database 192 may be used to support a variant search engine, into which one or more characteristics may be input and any variant(s) having the input characteristics may be reported to a user.

In some embodiments, the systems and methods described herein may be used to analyze BAM data. In other embodiments, the systems and methods described herein may be used to analyze raw FastQ data.

Figure 4:
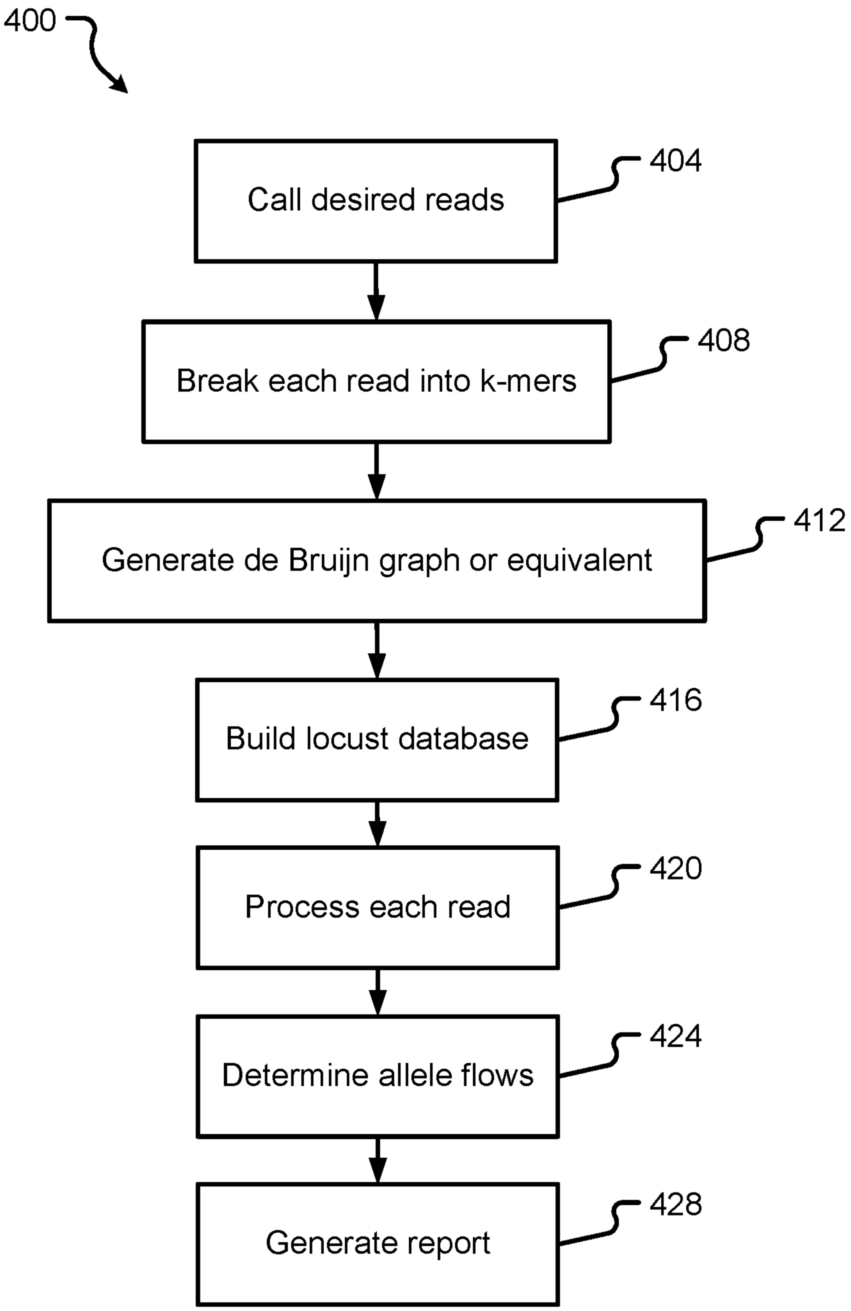
FIG. 4 is a flow chart depicting a variant calling method in accordance with at least some embodiments of the present disclosure.

Turning now to FIG. 4, a method 400 according to embodiments of the present disclosure comprises calling desired sequence reads (step 404). The reads may be from the same or a similar genomic location in a plurality of sources (e.g., patients, genes, etc.). The reads may be known or recurrent somatic mutations in key genes, such as KRAS, TPF3, etc.; pathogenic or likely pathogenic germline variants, such as BRCA1, BRCA2; and/or variants that are hard to call with usual methods, such as TYMS VNTR region, BRCA2 c.156_157insAlu. Each read may comprise a DNA sequence or an RNA sequence. The calling desired sequence reads may comprise precisely controlling the sequence variants that are callable, and may further comprise ignoring read alignments from bwa and other aligners. The calling desired sequence reads may be accomplished without utilizing any information such as RefSeq transcripts, a reference genome, etc. for analysis or annotation.

The method 400 comprises breaking each read into k-mers (step 408), where k is anywhere from 2 to at least 65. Each k-mer may be in the same format described above in connection with the k-mer subroutine 308.

The method 400 comprises generating a de Bruijn graph or an equivalent of the obtained DNA or RNA sequence and variants thereof (step 412). As described above in connection with the de Bruijn subroutine 312, the de Bruijn graph or equivalent may contain, for example, the k-mer edges of a given sequence; any k-mer edges that are changed by a single nucleotide variant of the sequence; any k-mer edges that are changed by a deletion in the original sequence; and any k-mer edges that are added by an insertion in the original sequence. As part of or in addition to generating the de Bruijn graph or equivalent, textual shorthand may be used to describe any identified variants.

The method 400 comprises building a locust database (step 416) that comprises a list of all k-mers from the de Bruijn graph or equivalent (e.g., the k-mers from the applicable DNA or RNA sequences). Each k-mer may be tagged to reflect whether the k-mer corresponds to the original sequence or a variant thereof. For k-mers corresponding to a variant, the tag may comprise a shorthand description of the variant in question. Building a locus database may additional comprise one or more aspects described above in connection with the database build subroutine 316.

The method 400 comprises processing each read (step 420) and counting the number of times each k-mer (including k-mers in the original sequence and k-mers in the variant sequences) appears. The k-mer count for each k-mer may be added to the database 192 or other database resulting from execution of the database build subroutine 316. In some embodiments, an identified k-mer that does not appear in any read, or that appears only in statistically insignificant number of reads, may be removed from the database. This should only occur with variant k-mers, as reference k-mers should appear in every non-variant instance of a given sequence.

The method 400 comprises determining allele flows (step 424). Determining allele flows comprises identifying junction k-mers, which are described above in connection with the allele flow subroutine 324, and then calculating the relative support (which is also described above in connection with the allele flow subroutine 324).

The method 400 comprises generating a report (step 428), which may be the same as or similar to any report that may be generated by the reporting subroutine 328 described above.

Figure 10:
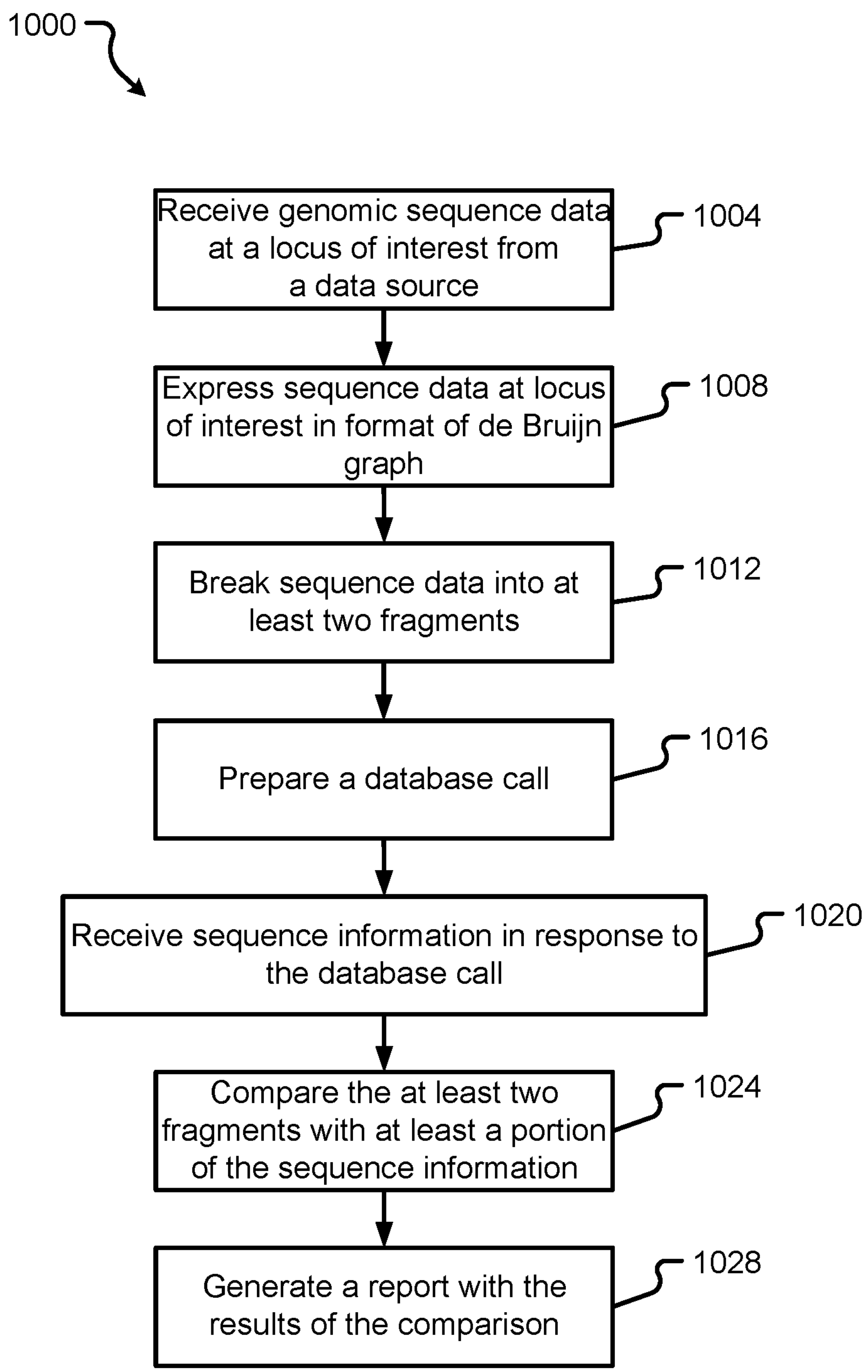
FIG. 10 is a flow chart depicting another variant calling method in accordance with at least some embodiments of the present disclosure.

With reference now to FIG. 10, a method 1000 according to at least some embodiments of the present disclosure comprises receiving genomic sequence data at a locus of interest from a data source (step 1004). The data source may be, for example, a database such as the database 172, or the database 160, or the database 156. The data source contains sequence data corresponding to a person or any other living organism.

The method 1000 also comprises expressing sequence data at a locus of interest in the format of a de Bruijn graph (step 1008). The format may be, for example, the format shown in FIG. 5, or an expression in software code or text of the format shown in FIG. 5. The expressing sequence data at a locus of interest in the format of a de Bruijn graph may comprise one or more of the aspects described above in connection with the de Bruijn subroutine 312.

The method 1000 also comprises breaking the sequence data into at least two fragments (step 1008). Each fragment may satisfy one or more predetermined criteria. For example, each fragment may correspond to at least two k-mers (step 1008). The k-mers may be identified using a k equal to anywhere from 2 to at least 65. Breaking the sequence data into fragments beneficially reduces the amount of processing time required to analyze the sequence data. As may be appreciated, if the sequence data comprise only four k-mers and each fragment must comprise at least two k-mers, then the fragments may be selected such that each fragment has two k-mers. If the sequence data comprise three or fewer k-mers, then a lower k may be necessary to increase the number of k-mers in the sequence data to satisfy a predetermined criterion for minimum number of k-mers. For example, if the sequence data have only three k-mers identified for k equal to 4, then changing k from 4 to 2 will increase the number of k-mers from three to five, allowing for one fragment with two k-mers and one fragment with three k-mers. The fragments may be selected so that the fragments have an approximately equal number of k-mers (e.g., for sequence data with nine k-mers, a first fragment may be selected with four k-mers and a second fragment may be selected with five k-mers), or the fragments may be selected so that as many fragments as possible have at least a predetermined number of k-mers (e.g., for sequence data with nine k-mers, each of a first, second, and third fragment may have two k-mers, and a fourth fragment may have three k-mers).

The method 1000 also comprises preparing a database call (step 1016). The database call may be prepared for transmission via a database interface such as the database interface 152. In some embodiments, the database call may comprise a call for sequence information at a locus of interest. The sequence information may be a reference sequence at the locus of interest. The sequence information may be in the format of a de Bruijn graph.

The method 1000 also comprises receiving sequence information in response to the database call (step 1020). The sequence information may be the requested sequence information. For example, the sequence information may be sequence information at a locus of interest. The sequence information may be a reference sequence at the locus of interest. The sequence information may be in the format of a de Bruijn graph. The sequence information may be received from a database, and the database may describe a genomic or transcriptomic locus of interest. In some embodiments, the database comprises sequence information for a reference sequence of the locus of interest in the format of a de Bruijn graph. Also in some embodiments, the database comprises sequence information for at least one variant sequence of the locus of interest in the format of a de Bruijn graph. The sequence information for the at least one variant sequence of the locus of interest may comprise at least two predetermined fragments. Each predetermine fragment may comprise at least two k-mers. Each predetermined fabric may be unique and specific to the at least one variant.

The method 1000 also comprises comparing the at least two fragments with at least a portion of the sequence information (step 1024). Where the sequence information is a reference sequence at the locus of interest, the comparing may comprise comparing the at least two fragments with at least a portion of the reference sequence at the locus of interest. The comparing may comprise matching the sequence data fragments with the sequence information received in response to the database call.

The method 1000 also comprises generating a report with the results of the comparison (step 1028). The report may call the sequence data as a variant sequence with which the sequence data has the highest count of k-mers. In other words, the report may identify the sequence data as corresponding to a variant sequence in the sequence information received from the database that shares the highest count of k-mers with the sequence data. The report may comprise any other information described herein as being contained within or useful to a report.

The following Examples are provided for the purposes of illustration and are not intended to limit the scope of the invention.

Example 1

This Example illustrates the use of a variant calling system as disclosed herein on clinical samples of tumor and normal DNA files for mutations of the TP53 gene (encodes tumor protein p53) from the Catalogue Of Somatic Mutations In Cancer (COSMIC) database.

Figure 11:
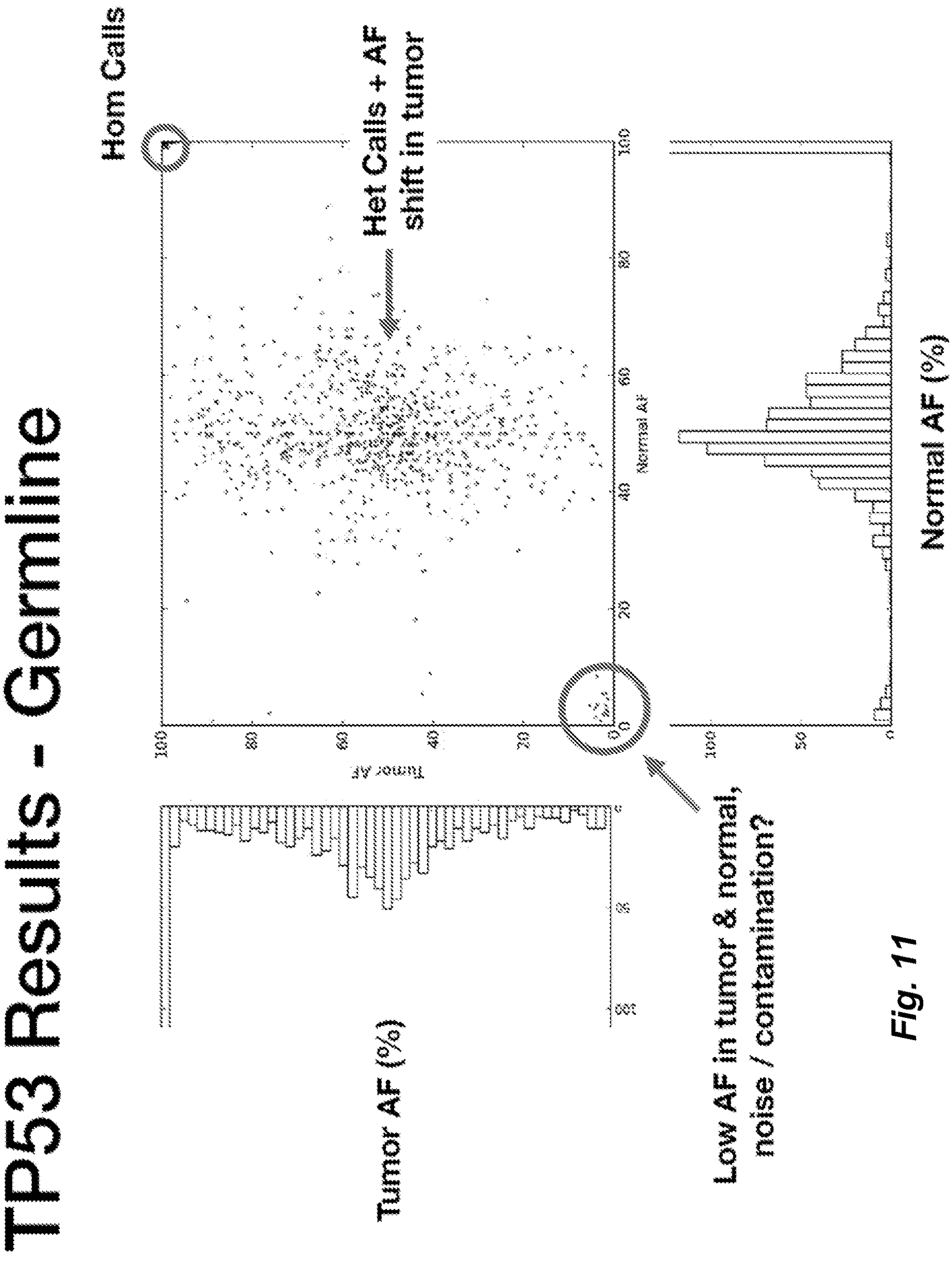
FIG. 11 shows a graph comparing normal allele flow with tumor allele flow in TP53 results in accordance with at least some embodiments of the present disclosure.

A variant calling database as disclosed herein was generated from 2,511 unique mutations spanning 12 exons of TP53 from the COSMIC database using a kmer length of 15 bp. A set of clinical data samples of tumor and normal DNA files was run against the database. The pipeline took about 37 minutes with maximum jobs set to 50 (0.6 s/BAM). The results are shown in FIG. 11, which reports the allele flow in normal and tumor samples. These results demonstrate the speed and effectiveness of the locus tester in identifying a large variety of TP53 somatic & germline variants (SNVs, insertions, deletions, and MNVs) within a wide range of allele fractions (i.e. allele flow) in thousands of tumor and matched-normal samples.

Figure 12:
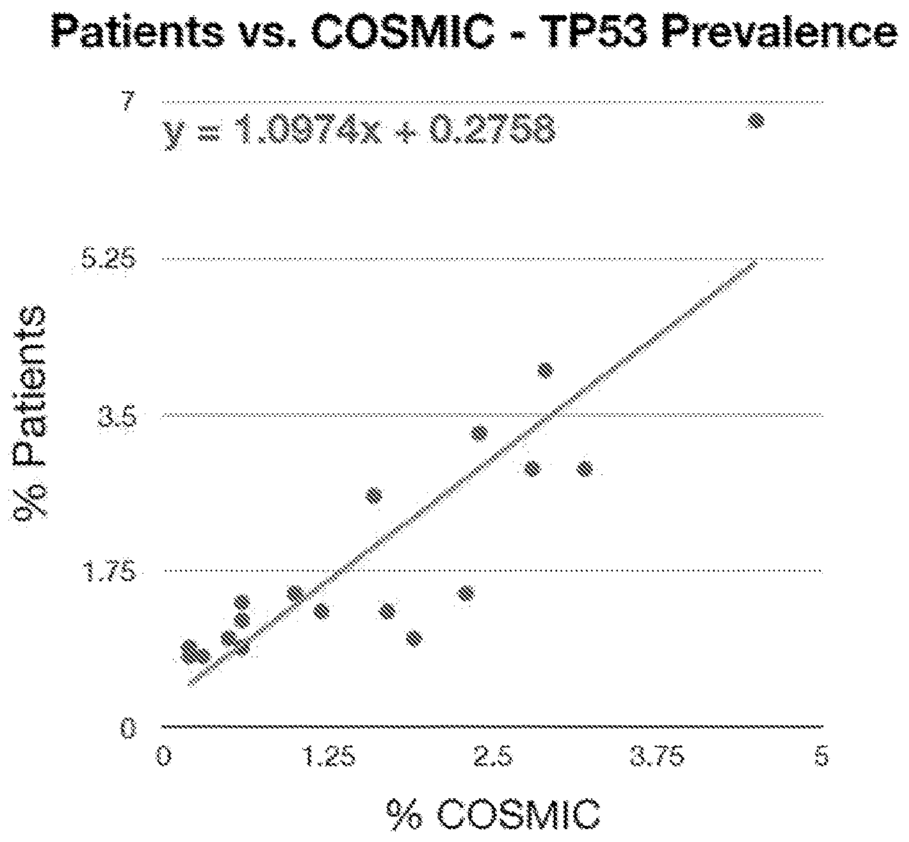
FIG. 12 shows a comparison of the prevalence of various TP53 variants between the COSMIC database and clinical samples in accordance with at least some embodiments of the present disclosure.

A comparison of the prevalence of various TP53 variants between the COSMIC database and the clinical samples is shown below in Table 1 and in FIG. 12.

TABLE 1

| TP53 Variant | # Patients % | # COSMIC % |
|---|---|---|
| c.524G > A, p.R175H | 53 6.8 | 730 4.5 |
| c.818G > A, p.R273H | 31 4.0 | 470 2.9 |
| c.817C > T, p.R273C | 26 3.3 | 396 2.4 |
| c.743G > A, p.R248Q | 23 2.9 | 524 3.2 |
| c.742C > T, p.R248W | 23 2.9 | 459 2.8 |
| c.637C > T, p.R213* | 20 2.6 | 262 1.6 |
| c.844C > T, p.R282W | 12 1.5 | 376 2.3 |
| c.586C > T, p.R196* | 12 1.5 | 162 1.0 |
| c.916C > T, p.R306* | 11 1.4 | 105 0.6 |
| c.733G > A, p.G245S | 10 1.3 | 274 1.7 |
| c.659A > G, p.Y220C | 10 1.3 | 204 1.2 |
| c.527G > T, p.C176F | 9 1.2 | 103 0.6 |
| c.747G > T, p.R249S | 8 1.0 | 303 1.9 |
| c.722C > T, p.S241F | 8 1.0 | 78 0.5 |
| c.574C > T, p.Q192* | 8 1.0 | 85 0.5 |
| c.734G > A, p.G245D | 7 0.9 | 93 0.6 |
| c.581T > G, p.L194R | 7 0.9 | 31 0.2 |
| c.488A > G, p.Y163C | 7 0.9 | 95 0.6 |
| c.991C > T, p.Q331* | 6 0.8 | 25 0.2 |
| c.734G > T, p.G245V | 6 0.8 | 51 0.3 |
| TOTAL | 780 | 16347 |

Table 1 shows the prevalence of TP53 variants in the clinical sample and in the COSMIC database. These data are shown in FIG. 2, which illustrates that the prevalence of TP53 variants in the clinical data is consistent with the prevalence of TP53 variants in the COSMIC database.

Example 2

Figure 13:
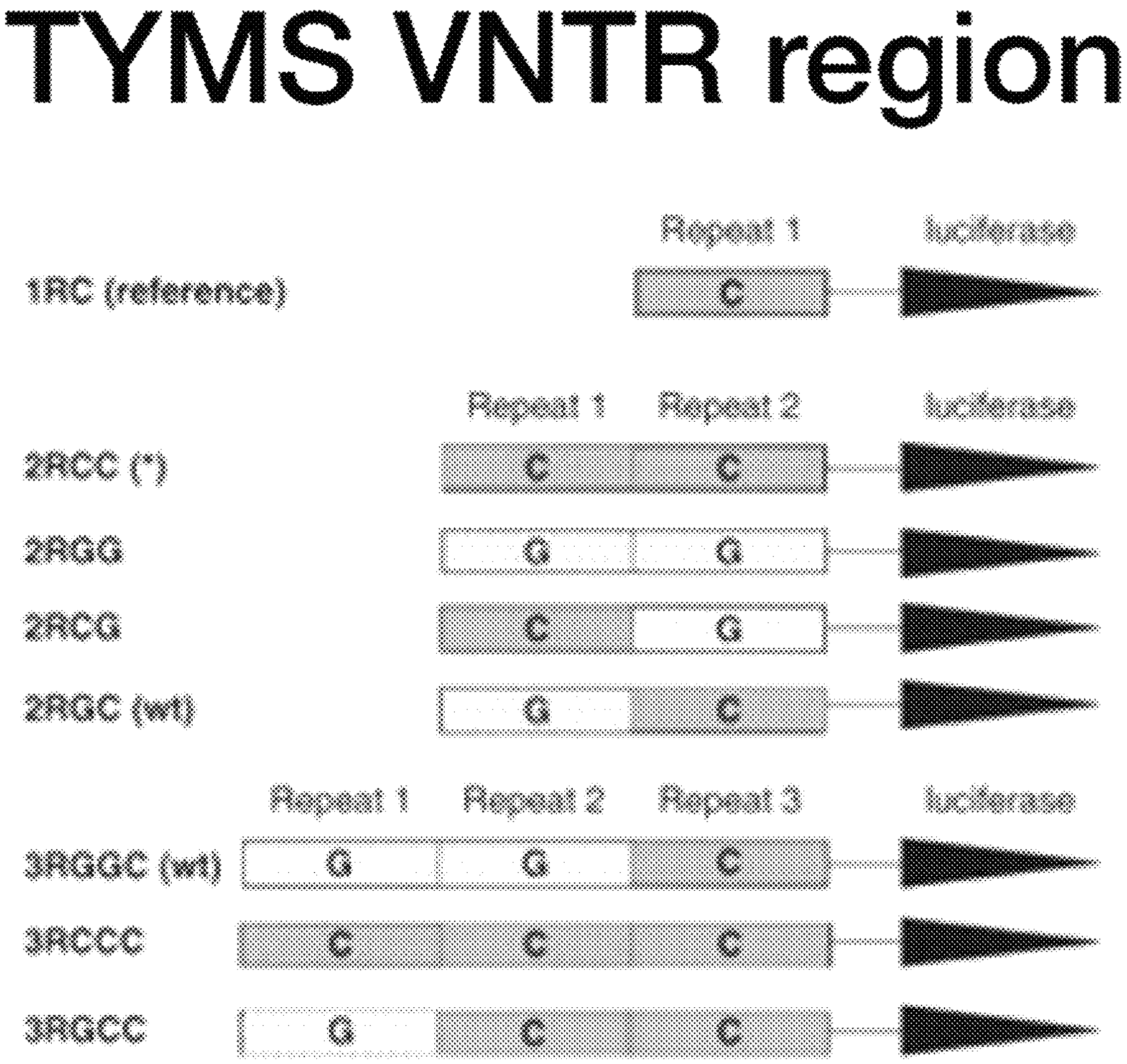
FIG. 13 shows potential TYMS VNTR variants in accordance with at least some embodiments of the present disclosure.

This Example illustrates the use of a variant calling system as disclosed herein on clinical samples of tumor and normal DNA files for alleles in the TYMS gene (encodes thymidylate synthetase). Variants in TYMS can include a variable number tandem repeat (VNTR) of a 28 bp repeat in the 5' untranslated promoter region of TYMS which may include a G>C substitution at the twelfth base of the repeat. The potential variants are shown in FIG. 13. VNTR variants of TYMS are linked to 5-FU toxicity, specifically, 2R/2R is linked to 43% likelihood of grade 3/4 toxicity; 2R/3R is linked to 18% likelihood of grade 3/4 toxicity; and 3R/3R is linked to 3% likelihood of grade 3/4 toxicity.

A variant calling database as disclosed herein was generated from a FASTA file containing the five TYMS alleles: 2RCC, 2RGC, 3RCCC, 3RGCC, 3RGGC using a kmer length of 65 bp. A set of clinical data samples of tumor and normal DNA files from 1,877 patients was run against the database. The pipeline took about 30 minutes with maximum jobs set to 50 (=0.5 s per BAM). The allele frequencies are shown in FIG. 14 and the genotype frequencies are shown in FIG. 15. These results demonstrate how the locus tester can be used to discover the presence of multiple complex variants in patient samples that are very difficult for traditional aligners and variant calling approaches, providing results which match up very well with known population allele frequencies of the TYMS alleles. These results also demonstrate that the locus tester can quickly identify patients likely to have the 2R/2R genotype, which is associated with strong toxicity of 5-FU therapy.

Example 3

This Example illustrates the use of a variant calling system as disclosed herein on a normal whole genome sequencing data set that was spiked with two difficult BRCA2 variants at about 50% allele frequency: 126 bp deletion: BRCA2 c.8975_9100del126 and 282 bp Alu insertion: BRCA2 c.156_157insAlu.

A variant calling database as disclosed herein was generated containing 8,763 germline variants (2,870 of which are pathogenic or likely pathogenic and 5,893 of which are uncertain significance, likely benign, benign or conflicting) using a kmer length of 15 bp. A set of clinical data samples of tumor and normal DNA files was run against the database. The pipeline took about one hour, twenty minutes with maximum jobs set to 50 (=1.3 s per BAM). There were no occurrences of the two difficult BRCA2 variants in the clinical data. Then a normal WGS data set that was spiked with the two BRCA2 variants at about 50% allele frequency. The pipeline took about six seconds. These results demonstrate three things. Firstly, these results demonstrate the speed and effectiveness of the locus testing for germline BRCA2 variants in thousands of patients (akin to the TP53 experiment above). Secondly, these results demonstrate that one can use the same locus testing model to search for difficult/complex variants. Finally, the use of in silico simulated data proves that the locus tester can find variants when they are present in the data, thus increasing confidence that a patient does not have a given allelic variant when the locus tester finds no evidence of the variant's presence in the patient sequence data.

Example 4

This Example illustrates the use of a variant calling system as disclosed herein to identify gene fusions. A variant calling database as disclosed herein was generated comprising 301 gene fusions, EGFRvIII, and MET exon 14 skip, a total of 303 fusions, plus Sarcoma-associated fusions were downloaded from the COSMIC database. The system included, for each gene pair, every combination of exons that produces a potentially functional fusion (a single ORF (Methionine Start→Stop codon, no Stops in the middle); novel Met start codons can be used if they satisfy the above; and all isoforms are used, but only unique, non-canonical pairings were added to the database). The database included about 250 Mb, used a kmer length of 25 and took about 50 minutes per BAM to check for all fusions, resulting in 41,865 unique exon pairings of 849 RefSeq isoforms (350 genes). The database calls fusions from RNA sequencing data (local transcript BAMS) but does not handle RNA differently from DNA.

Figure 16:
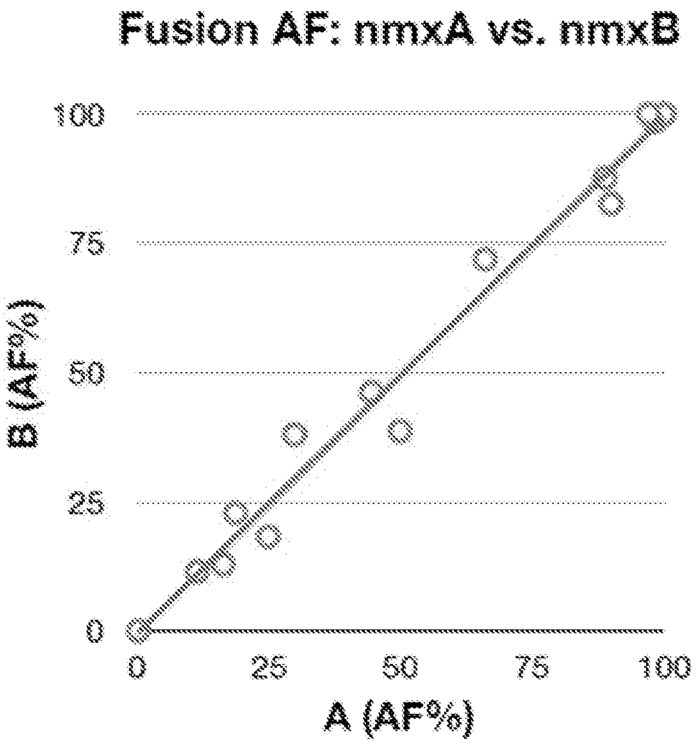
FIG. 16 shows a graph of results from a database call of 16 common oncogenic fusions over a wide range of expressed allele flows (0.35%-100%) with nothing else being called, in accordance with at least some embodiments of the present disclosure.

SeraCare (of Milford, MA) has controls featuring 16 common oncogenic fusions. The database called all of these 16 fusions over a wide range of expressed allele flows (0.35%-100%) with nothing else being called. The results for this are shown below in Table 2 and FIG. 16.

TABLE 2

| Fusion | Variant Call | nmxA AF | nmxB AF |
|---|---|---|---|
| 1 EML4-ALK | EML4(NM_019063): ex13-ALK(NM_004304): ex20 | 50.00 | 38.89 |
| 2 KIF5B-RET | KIF5B(NM_004521): ex24-RET(NM_020975): ex11 | 16.44 | 13.23 |
| 3 NCOA4-RET | NCOA4(NM_001145260): ex8-RET(NM_020975): ex12 | 11.54 | 11.80 |
| 4 CD74-ROS1 | CD74(NM_001025159): ex6-ROS1(NM_002944): ex34 | 0.35 | 0.41 |
| 5 SLC34A2-ROS1 | SLC34A2(NM_006424): ex4-ROS1(NM_002944): ex34 | 100.00 | 100.00 |
| 6 TPM3-NTRK1 | TPM3(NM_153649): ex7-NTRK1(NM_002529): ex10 | 90.00 | 82.76 |
| 7 FGFR3-BAIAP2L1 | FGFR3(NM_000142): ex17-BAIAP2L1(NM_018842): ex2 | 66.15 | 72.00 |
| 8 PAX8-PPARG | PAX8(NM_003466): ex9-PPARG(NM_015869): ex2 | 88.89 | 87.67 |
| 9 FGFR3-TACC3 | FGFR3(NM_000142): ex17-TACC3(NM_006342): ex11 | 25.00 | 18.54 |
| 10 ETV6-NTRK3 | ETV6(NM_001987): ex5-NTRK3(NM_001012338): ex15 | 30.00 | 38.24 |
| 11 LMNA-NTRK1 | LMNA(NM_005572): ex2-NTRK1(NM_002529): ex11 | 18.80 | 23.08 |
| 12 SLC45A3-BRAF | SLC45A3(NM_033102): ex1-BRAF(NM_004333): ex8 | 44.58 | 46.39 |
| 13 TMPRSS2-ERG | TMPRSS2(NM_005656): ex1-ERG(NM_001136154): ex2 | 100.00 | 100.00 |
| 14 EGFR-SEPT15 | EGFR(NM_005228): ex24-SEPT14(NM_207366): ex10 | 98.36 | 98.55 |
| 15 MET Ex. 14 Skip | MET(NM_001127500): ex13-MET(NM_001127500): ex15 | 100.00 | 100.00 |
| 16 EGFRvIII | EGFR(NM_005228): ex1-EGFR(NM_005228): ex8 | 97.14 | 100.00 |

The variant calling database of this example was run on 1,264 clinical RNA BAMs streamed from a secure data storage system with maxjobs set at 50. The query ran for about 36 hours and detected 148 fusions. The top 20 fusions—as measured by read coverage of the fusion sequence formed by the specific junction of the two genes—are shown below in Table 3 with the most prevalent being shown in Table 4.

TABLE 3

| Fusion | Coverage | AF % | Cancer Type | Expected? | Reported? |
|---|---|---|---|---|---|
| EGFR-SEPT14 | 2013.17 | 94 | Glioblastoma Yes No (old gps) | | |
| EGFRvIII | 902.23 | 84.32 | Glioblastoma | Yes | Yes |
| EGFR-SEPT14 | 882.91 | 94.02 | Astrocytoma | Yes | Yes |
| NAB2-STAT6 | 647.32 | 76.49 | Kidney Sarcoma | Yes | No (not panel) |
| HNRNPA2B1-ETV1 | 570.14 | 71.71 | Prostate CA | Yes | Yes |
| DNAJB1-PRKACA | 547.68 | 84.02 | Multifocal Fibrolamellar Carcinoma | Yes | No (old gps) |
| EGFRvIII | 519.19 | 47.73 | Glioblastoma | Yes | Yes |
| COL1A1-PDGFB | 506.14 | 38.19 | Breast Cancer/Spindle Cell Met. | Yes | Yes |
| FGFR3-TACC3 | 450.86 | 59.56 | Lung cancer | Yes | Yes |
| EGFRvIII | 393.42 | 29.09 | Glioblastoma | Yes | Yes |
| NDRG1-ERG | 383.7 | 37.36 | Prostate CA | Yes | Yes |

TABLE 3-continued

| Fusion | Coverage | AF % | Cancer Type | Expected? | Reported? |
|---|---|---|---|---|---|
| MYB-NFIB | 364 | 85.55 | Adenoid Cystic Carcinoma | Yes | No (not panel) |
| EGFRvIII | 345.77 | 32.9 | Glioblastoma | Yes | Yes |
| COL1A1-PDGFB | 337.36 | 31.73 | Dermatofibrosarcoma Protuberans | Yes | Yes |
| MYB-NFIB | 312.86 | 84.84 | Adenoid Cystic Carcinoma | Yes | Yes |
| SS18-SSX1 | 302.21 | 75.22 | Metastatic Synovial Sarcoma | Yes | No (not panel) |
| FGFR3-TACC3 | 269.95 | 46.44 | Esophageal Cancer | Yes | Yes |
| MYB-NFIB | 257.71 | 87.15 | Adenoid Cystic Carcinoma | Yes | Yes |
| COL1A1-PDGFB | 247.64 | 25.5 | Dermatofibrosarcoma Protuberans | Yes | Yes |
| MYB-NFIB | 215 | 46.75 | Adenoid Cystic Carcinoma | Yes | No (not panel |

+128 more

TABLE 4

| Fusion | Count |
|---|---|
| MYB-NFIB | 14 |
| SLC45A3-ELK4 | 12 |
| EWSR1-FLI1 | 11 |
| EGFRvIII | 8 |
| TMPRSS2-ERG | 7 |
| FGFR3-TACC3 | 6 |
| COL1A1-PDGFB | 6 |
| VTI1A-TCF7L2 | 5 |
| SS18-SSX4 | 5 |
| NAB2-STAT6 | 5 |
| MET Exon 14 Skip | 5 |
| EWSR1-ATF1 | 4 |
| EGFR-SEPT14 | 4 |
| DHH-RHEBL1 | 4 |
| HEY1-NCOA2 | 3 |
| EML4-ALK | 3 |
| CTAGE5-GEMIN2 | 3 |
| PAX3-FOXO1 | 2 |
| NFIX-MAST1 | 2 |
| HNRNPA2B1-ETV1 | 2 |

+20 more

The variant calling database of this example had high sensitivity. COL1A1-PDGFB is a rare fusion that characterizes Dermatofibrosarcoma Protuberans, a spindle cell tumor that is sometimes misdiagnosed as a breast cancer. The variant calling database was able to identify contaminated samples, i.e., samples having coverage of less than 2× and allele flow of less than 1%.

Example 5

This Example illustrates the use of a variant calling system as disclosed herein to identify mitochondrial haplogroups. A variant calling database as disclosed herein was generated comprising 1,239 mitochondrial complete genomes, each representing one haplogroup. Each genome was about 16 kb (+100 bp circularization), the kmer length was 45 bp and the size of the database was 325 Mb. The database was tested with four samples of known haplogroups and the top hit correctly identified the known haplogroup. The results of this testing are shown in Table 5.

TABLE 5

| Sample | Type | Known Haplogroup | Top Locust Hit (NCBI ID-Haplogroup) | Coverage | % Covered |
|---|---|---|---|---|---|
| BJ Fibroblast | MiSeq (300 bp) | K1c1 | HQ398201.1-K1c1 | 103.03 | 99.1% |
| Rando #1 | WGS | J1c | FJ499471.1-J1c | 1066.52 | 99.6% |

TABLE 5-continued

| Sample | Type | Known Haplogroup | Top Locust Hit (NCBI ID-Haplogroup) | Coverage | % Covered |
|---|---|---|---|---|---|
| Rando #2 | WGS | H7 | JQ253591.1-H7 | 1057.81 | 99.6% |
| Related to Rando #2 | WGS | H7 | JQ253591.1-H7 | 1051.39 | 99.7% |

The variant calling database of this example was further tested with a set of clinical data. The processing time was about 1.5 hours for 3,755 BAMs. The results of this analysis are shown in Table 6 and Table 7.

TABLE 6

| Sample | Status | Haplo (N) | Haplo (T) |
|---|---|---|---|
| RKwJwkeiAXWWqqaPLHLszQ | PERFECT | B2 | B2 |
| AHSuZt7MFoqynqh4pQtPM7 | PERFECT | H3 | H3 |
| YzhJ5Yx2MjBYQPo9sBbtaj | PARTIAL-1x | H3 | H* |
| YtZeygAzEcpFPr8pvic6oU | PERFECT | J2a1a1b | J2a1a1b |
| ZaWerZU2zXokytdtE8aGDB | PERFECT | U5a | U5a |
| nAMhgFFVAxMpZnr6ePEBpH | PERFECT | HV* | HV* |
| kLTSj5AC3x5NjtqtGZXEZU | PERFECT | HV* | HV* |
| Z4X465ZzYy2JW5qkkZzesP | PERFECT | H | H |
| Pxh838HVcfqzkkGhECKsW7 | PERFECT | A10 | A10 |
| c8bGsQS6ijf9NkyxgFSTjT | PARTIAL-1x | I2 | I |
| T6J87KhJjGCDPLJPrR9LBd | PARTIAL-3x | U5a | U5a2a |
| gDszCdpEJJXo4fiyY9FAQ9 | PERFECT | K1a10 | K1a10 |
| rqrSbAAnhT6c8SJhbMb8c | PARTIAL-4x | U5a1a1 | U5a1 |
| rMirAFhJsMJnBReNcZThRP | PERFECT | J1b1a1 | J1b1a1 |
| mZBTdJ5v33zALkK64WeP9C | PERFECT | T2b4a1 | T2b4a1 |
| MDS5tu9csN4pNHjrjbsDFT | PARTIAL-5x | H13a1 | H13a1a1 |
| kf88Waq4P33aMR9vGYKeka | PERFECT | K1c2 | K1c2 |

Processing Time ~1.5 h for 3,755 BAMs

TABLE 7

| Status | Count | |
|---|---|---|
| MISS | 10 | Improving |
| PARTIAL-1x | 24 | T-N Matches |
| PARTIAL-2x | 19 | ↓ |
| PARTIAL-3x | 20 | |
| PARTIAL-4x | 9 | |
| PARTIAL-5x | 2 | |
| PERFECT | 1227 | |
| TOTAL | 1311 | |

* Normal & Tumor > 100x coverage

Note:
All PARTIAL matches get haplogroup root (e.g. "H", "U", etc.) correct:
99.2% Root Match (e.g. H = H)
97.4% >= 2-digit Match (e.g. H1 = H1a)
96.0% >= 3-digit Match (e.g. U5a = U5a2a)
MISSes:
5/10 mismatches were ranked 1st/2nd
9/10 mismatches within top 5

Figure 17:
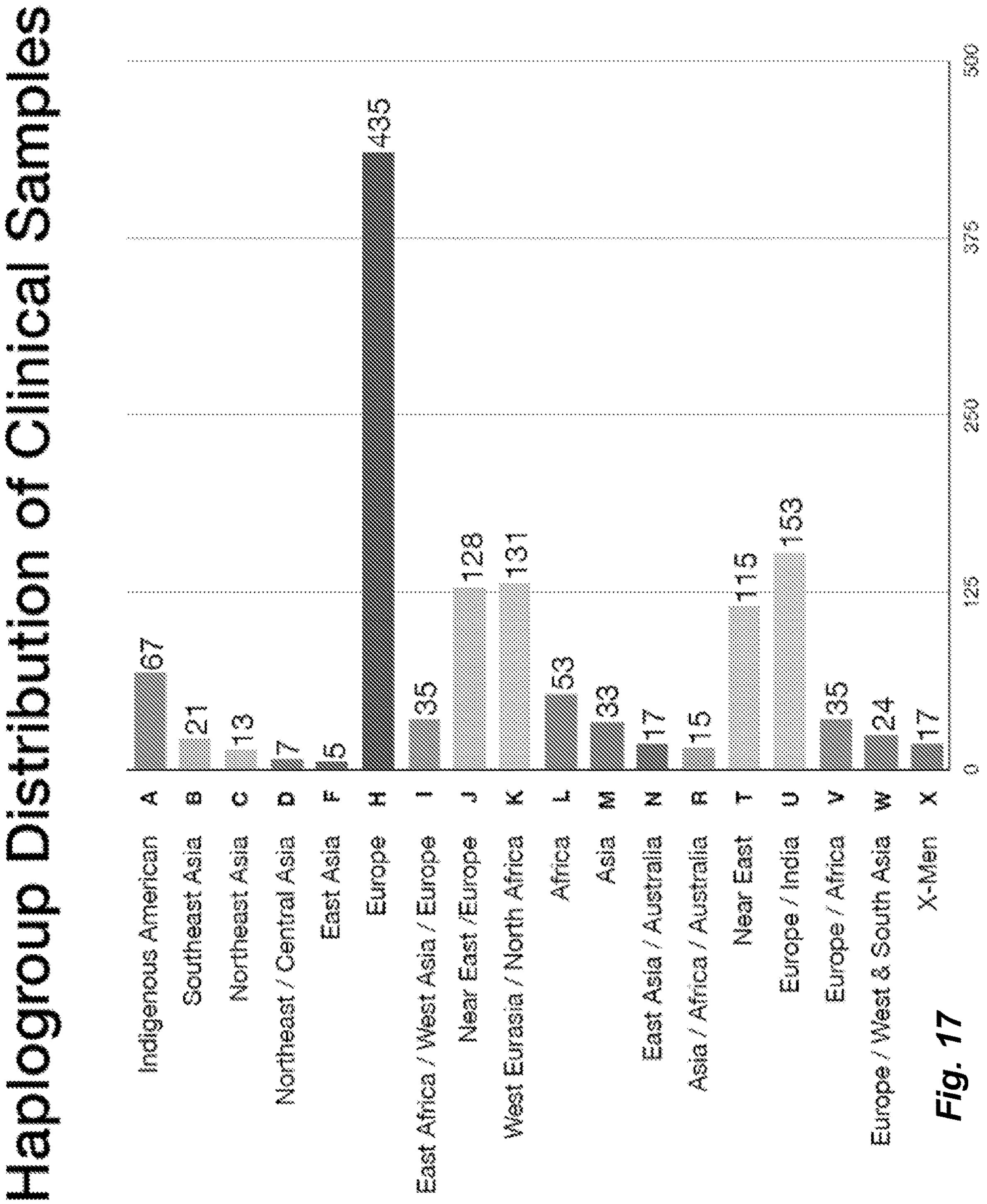
FIG. 17 shows a haplogroup distribution of clinical samples in accordance with at least some embodiments of the present disclosure.

The results show 1227/1311 correctly identified mitochondrial haplogroups in the sample, 74/1311 partial matches in which a haplogroup root (e.g., "H", "U", etc.) was correctly identified, and 10/1311 misses. The haplogroup distribution of the clinical samples is illustrated in FIG. 17.

Further to the foregoing description and examples, in some embodiments patient results may be updated in real time based on the latest (e.g., the most updated) version of the locust database 192 as they come through a lab. The patient database 172 may be updated with new or updated locusts from the locust database 192. The updating may or may not occur as a background process. The updating may comprise identifying patients that need to be run on a new or updated locust; running the patient(s) through the new or updated locust (which be accomplished in parallel on cluster); and updating the patient database with results. Information regarding the variants may also be updated or added, including improving or fixing annotations, flagging or removing artifact variants, and linking variants to external databases (ClinVar). A results table may be used to feed a dashboard or website, which may be used to present statistics on variants, and/or to identify variants in certain patient groups (e.g., groups by disease type).

The discussion herein provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

---

What is claimed is:

1. A method of variant calling of genomic or transcriptomic sequence data at a locus of interest, comprising:

a) matching sequence data fragments against a database describing a genomic or transcriptomic locus of interest, wherein the sequence data fragments are formed by breaking a de Bruijn graph format of the sequence data at the locus of interest into the at least two fragments, each comprising at least two k-mers, and wherein the database comprises one or more non-transitory computer readable storage media on which:

i) sequence information is stored for a reference sequence of the locus in the format of a de Bruijn graph;

ii) sequence information is stored for at least one variant sequence of the locus in the format of a de Bruijn graph; wherein the sequence information for at least one variant sequence of the locus comprises the at least two fragments, wherein each fragment comprises at least two k-mers, wherein each k-mer is tagged in the database to reflect whether the k-mer corresponds to an original sequence or a variant thereof, wherein each fragment is unique and is specific to the at least one variant, wherein each fragment is selected to satisfy one or more predetermined criteria, and wherein a number of k-mers in the at least two k-mers is selected to satisfy a predetermined criterion for a minimum number of k-mers; and b) calling, from one or more databases, the sequence data as a variant sequence with which the sequence data has the highest count of k-mers.

2. The method of claim 1, wherein the sequence data is genomic sequence data.

3. The method of claim 1, wherein the sequence data is transcriptomic sequence data.

4. The method of claim 1, wherein the at least one variant sequence of the locus is de-identified.

5. The method of claim 1, wherein the at least one variant sequence is selected from the group consisting of single nucleotide variants, multiple nucleotide variants, insertions, deletions, gene fusions, and haplogroups.

6. The method of claim 1, further comprising identifying junction k-mers in the sequence data or the sequence information.

7. The method of claim 6, further comprising calculating a relative support at the identified junction k-mers.

8. A database describing a genomic or transcriptomic locus of interest, the database comprising one or more non-transitory computer readable storage media on which:

a) first sequence information is stored for a reference sequence of a locus in the format of a de Bruijn graph;

b) second sequence information is stored for at least one variant sequence of the locus in the format of a de Bruijn graph; wherein the sequence information for at least one variant sequence of the locus comprises at least two fragments and wherein each fragment is unique and is specific to the at least one variant, and wherein each fragment is selected to satisfy one or more predetermined criteria; and c) a list of all k-mers from the de Bruijn graph, wherein each k-mer in the list is tagged in to reflect whether the k-mer corresponds to an original sequence or a variant thereof, and wherein a number of k-mers in the list of all k-mers is selected to satisfy a predetermined criterion for a minimum number of k-mers.

9. The database of claim 8, further comprising a list of k-mer junctions.

10. The database of claim 8, further comprising a list of k-mers appearing in the first sequence information and the second sequence information.

11. The database of claim 10, further comprising a count corresponding to each k-mer in the list of k-mers, the count corresponding to the number of occurrences of the each k-mer in the first and second sequence information.

12. The database of claim 10, further comprising a variant tag corresponding to each k-mer in the list of k-mers.

13. The database of claim 12, wherein at least some of the variant tags identify the corresponding k-mers with the reference sequence.

14. The database of claim 12, wherein at least some of the variant tags identify the corresponding k-mers with a single nucleotide variant, a multiple nucleotide variant, an insert, a deletion, a gene fusion, or a haplogroup.

15. A server comprising:

a database interface;

a processor coupled with the database interface; and non-transitory computer-readable storage media coupled with the processor and comprising instructions stored thereon that, when executed by the processor, enable the processor to:

receive genomic sequence data from a data source;

format the genomic sequence data into a de Bruijn graph;

break the sequence data in the de Bruijn graph format into at least two fragments, wherein each fragment comprises at least two k-mers and satisfies one or more predetermined criteria, and wherein a number of k-mers in the at least two k-mers is selected to satisfy a predetermined criterion for a minimum number of k-mers;

prepare a database call for transmitting via the database interface, wherein the database call comprises a call for sequence information for a reference sequence of a locus of interest in the format of a de Bruijn graph, wherein the database stores the sequence information on one or more non-transitory computer readable storage media and also stores a list of k-mers on the one or more non-transitory computer readable storage media in which each k-mer is tagged in the database to reflect whether the k-mer corresponds to an original sequence or a variant thereof;

receive the sequence information via the database interface;

compare the at least two fragments with at least a portion of the reference sequence of the locus of interest; and transmit a report across a communication network via the database interface that includes results of the comparison of the at least two fragments with the at least a portion of the reference sequence of the locus of interest.

16. The server of claim 15, wherein the sequence information further comprises at least one variant sequence of the locus of interest.

17. The server of claim 16, wherein the sequence information comprises a count for each k-mer in the list of k-mers.

18. The server of claim 17, wherein the comparing comprises identifying matches between a set of k-mers in the at least two fragments and one or more k-mers in the list of k-mers.

19. The server of claim 18, wherein the report identifies the sequence data as corresponding to the reference sequence or the variant sequence based on the matching.

20. The server of claim 15, wherein the non-transitory computer-readable storage media comprises additional instructions that, when executed by the processor, further enable the processor to transmit the sequence data via the database interface.

* * * * *

SEQUENCE LISTING

```
<160> NUMBER OF SEQ ID NOS: 40

<210> SEQ ID NO 1
<211> LENGTH: 6
<212> TYPE: DNA
<213> ORGANISM: Artificial Sequence
<220> FEATURE:
<223> OTHER INFORMATION: Synthetic

<400> SEQUENCE: 1

attagc                                                                  6


<210> SEQ ID NO 2
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 2

atta                                                                    4


<210> SEQ ID NO 3
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 3

ttag                                                                    4


<210> SEQ ID NO 4
<211> LENGTH: 4
```

<212> TYPE: DNA
<213> ORGANISM: Artificial Sequence
<220> FEATURE:
<223> OTHER INFORMATION: Synthetic k-mer

<400> SEQUENCE: 4 tagc 4

<210> SEQ ID NO 5
<211> LENGTH: 5
<212> TYPE: DNA
<213> ORGANISM: Artificial Sequence
<220> FEATURE:
<223> OTHER INFORMATION: Synthetic k-mer

<400> SEQUENCE: 5 attag 5

<210> SEQ ID NO 6
<211> LENGTH: 5
<212> TYPE: DNA
<213> ORGANISM: Artificial Sequence
<220> FEATURE:
<223> OTHER INFORMATION: Synthetic k-mer

<400> SEQUENCE: 6 ttagc 5

<210> SEQ ID NO 7
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 7 catt 4

<210> SEQ ID NO 8
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 8 attt 4

<210> SEQ ID NO 9
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 9 tttt 4

<210> SEQ ID NO 10
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 10

```
tttc                                                                    4


<210> SEQ ID NO 11
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 11

ttcg                                                                    4


<210> SEQ ID NO 12
<211> LENGTH: 12
<212> TYPE: DNA
<213> ORGANISM: Artificial Sequence
<220> FEATURE:
<223> OTHER INFORMATION: Synthetic k-mer

<400> SEQUENCE: 12

attttttttt tc                                                          12


<210> SEQ ID NO 13
<211> LENGTH: 10
<212> TYPE: DNA
<213> ORGANISM: Artificial Sequence
<220> FEATURE:
<223> OTHER INFORMATION: Synthetic

<400> SEQUENCE: 13

cattttttcg                                                             10


<210> SEQ ID NO 14
<211> LENGTH: 11
<212> TYPE: DNA
<213> ORGANISM: Artificial Sequence
<220> FEATURE:
<223> OTHER INFORMATION: Synthetic

<400> SEQUENCE: 14

atatgcattc g                                                           11


<210> SEQ ID NO 15
<211> LENGTH: 11
<212> TYPE: DNA
<213> ORGANISM: Artificial Sequence
<220> FEATURE:
<223> OTHER INFORMATION: Synthetic

<400> SEQUENCE: 15

atctgcattc g                                                           11


<210> SEQ ID NO 16
<211> LENGTH: 10
<212> TYPE: DNA
<213> ORGANISM: Artificial Sequence
<220> FEATURE:
<223> OTHER INFORMATION: Synthetic k-mer

<400> SEQUENCE: 16

atatgattcg                                                             10


<210> SEQ ID NO 17
<211> LENGTH: 21
<212> TYPE: DNA
<213> ORGANISM: Artificial Sequence
```

```
<220> FEATURE:
<223> OTHER INFORMATION: Synthetic

<400> SEQUENCE: 17

atatgcatta ggctatggtc g                                            21


<210> SEQ ID NO 18
<211> LENGTH: 10
<212> TYPE: DNA
<213> ORGANISM: Artificial Sequence
<220> FEATURE:
<223> OTHER INFORMATION: Synthetic

<400> SEQUENCE: 18

aggctatggt                                                         10


<210> SEQ ID NO 19
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 19

atat                                                                4


<210> SEQ ID NO 20
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 20

tatg                                                                4


<210> SEQ ID NO 21
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 21

atgc                                                                4


<210> SEQ ID NO 22
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 22

atcc                                                                4


<210> SEQ ID NO 23
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 23

tctg                                                                4
```

<210> SEQ ID NO 24
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 24 atga 4

<210> SEQ ID NO 25
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 25 tgat 4

<210> SEQ ID NO 26
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 26 tagg 4

<210> SEQ ID NO 27
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 27 tagg 4

<210> SEQ ID NO 28
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 28 atgg 4

<210> SEQ ID NO 29
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 29 tggt 4

<210> SEQ ID NO 30
<211> LENGTH: 7
<212> TYPE: DNA
<213> ORGANISM: Artificial Sequence
<220> FEATURE:
<223> OTHER INFORMATION: Synthetic

<400> SEQUENCE: 30 atgcatt 7

<210> SEQ ID NO 31
<211> LENGTH: 6
<212> TYPE: DNA
<213> ORGANISM: Artificial Sequence
<220> FEATURE:
<223> OTHER INFORMATION: Synthetic

<400> SEQUENCE: 31 atgatt 6

<210> SEQ ID NO 32
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 32 gatt 4

<210> SEQ ID NO 33
<211> LENGTH: 5
<212> TYPE: DNA
<213> ORGANISM: Artificial Sequence
<220> FEATURE:
<223> OTHER INFORMATION: Synthetic k-mer

<400> SEQUENCE: 33 aaatg 5

<210> SEQ ID NO 34
<211> LENGTH: 7
<212> TYPE: DNA
<213> ORGANISM: Artificial Sequence
<220> FEATURE:
<223> OTHER INFORMATION: Synthetic k-mer

<400> SEQUENCE: 34 gcatcgg 7

<210> SEQ ID NO 35
<211> LENGTH: 5
<212> TYPE: DNA
<213> ORGANISM: Artificial Sequence
<220> FEATURE:
<223> OTHER INFORMATION: Synthetic k-mer

<400> SEQUENCE: 35 atttg 5

<210> SEQ ID NO 36
<211> LENGTH: 5
<212> TYPE: DNA
<213> ORGANISM: Artificial Sequence
<220> FEATURE:
<223> OTHER INFORMATION: Synthetic k-mer

<400> SEQUENCE: 36 tatac 5

<210> SEQ ID NO 37

-continued

```
<211> LENGTH: 5
<212> TYPE: DNA
<213> ORGANISM: Artificial Sequence
<220> FEATURE:
<223> OTHER INFORMATION: Synthetic k-mer

<400> SEQUENCE: 37

cggga                                                                 5


<210> SEQ ID NO 38
<211> LENGTH: 6
<212> TYPE: DNA
<213> ORGANISM: Artificial Sequence
<220> FEATURE:
<223> OTHER INFORMATION: Synthetic k-mer

<400> SEQUENCE: 38

taaaac                                                                6


<210> SEQ ID NO 39
<211> LENGTH: 6
<212> TYPE: DNA
<213> ORGANISM: Artificial Sequence
<220> FEATURE:
<223> OTHER INFORMATION: Synthetic k-mer

<400> SEQUENCE: 39

catctg                                                                6


<210> SEQ ID NO 40
<211> LENGTH: 4
<212> TYPE: DNA
<213> ORGANISM: Artificial Sequence
<220> FEATURE:
<223> OTHER INFORMATION: Synthetic k-mer

<400> SEQUENCE: 40

aatg                                                                  4
```